(12) United States Patent
Covey et al.

(10) Patent No.: US 9,676,812 B2
(45) Date of Patent: *Jun. 13, 2017

(54) NEUROACTIVE 19-ALKOXY-17-SUBSTITUTED STEROIDS, PRODRUGS THEREOF, AND METHODS OF TREATMENT USING SAME

(71) Applicants: Washington University, St. Louis, MO (US); Sage Therapeutics, Inc., Cambrige, MA (US)

(72) Inventors: Douglas Covey, St. Louis, MO (US); Albert Jean Robichaud, Ringoes, NJ (US)

(73) Assignees: Washington University, St. Louis, MO (US); Sage Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/652,717

(22) PCT Filed: Dec. 18, 2013

(86) PCT No.: PCT/US2013/076214
§ 371 (c)(1),
(2) Date: Jun. 16, 2015

(87) PCT Pub. No.: WO2014/100228
PCT Pub. Date: Jun. 26, 2014

(65) Prior Publication Data
US 2015/0315230 A1  Nov. 5, 2015

Related U.S. Application Data

(60) Provisional application No. 61/738,822, filed on Dec. 18, 2012.

(51) Int. Cl.
| | | |
|---|---|---|
| C07J 1/00 | (2006.01) |
| C07J 5/00 | (2006.01) |
| C07J 7/00 | (2006.01) |
| C07J 21/00 | (2006.01) |
| C07J 41/00 | (2006.01) |
| C07J 51/00 | (2006.01) |

(52) U.S. Cl.
CPC ............ C07J 1/0029 (2013.01); C07J 1/0011 (2013.01); C07J 1/0018 (2013.01); C07J 5/0015 (2013.01); C07J 7/002 (2013.01); C07J 21/00 (2013.01); C07J 41/0005 (2013.01); C07J 41/0094 (2013.01); C07J 21/006 (2013.01); C07J 21/008 (2013.01); C07J 41/0016 (2013.01); C07J 51/00 (2013.01)

(58) Field of Classification Search
CPC ........ C07J 1/0018; C07J 21/00; C07J 21/008; C07J 41/0005; C07J 41/0016; C07J 41/0094; C07J 51/00; C07J 5/0015; C07J 5/002

USPC ......... 514/173, 178, 182; 552/522, 600, 632
See application file for complete search history.

(56) References Cited

U.S. PATENT DOCUMENTS

| | | | |
|---|---|---|---|
| 2,856,415 A | 10/1958 | Mihina | |
| 3,206,459 A | 9/1965 | Cross | |
| 4,071,625 A | 1/1978 | Grunwell et al. | |
| 4,179,336 A | 12/1979 | Weber et al. | |
| 4,389,345 A | 6/1983 | Lenz | |
| 5,925,630 A | 7/1999 | Upasani et al. | |
| 6,844,456 B2* | 1/2005 | Covey ................ | A61K 31/565 552/502 |
| 7,064,116 B2* | 6/2006 | Calogeropoulou .... | C07J 5/0015 514/177 |
| 7,781,421 B2* | 8/2010 | Covey ................. | C07J 53/00 514/172 |
| 8,759,330 B2* | 6/2014 | Covey ................. | C07J 53/00 514/172 |
| 9,156,876 B2* | 10/2015 | Covey ................ | A61K 31/565 |
| 2002/0091112 A1 | 7/2002 | Menzenbach et al. | |
| 2005/0176976 A1 | 8/2005 | Calogeropoulou et al. | |
| 2006/0094696 A1 | 5/2006 | Leese et al. | |
| 2009/0048218 A1 | 2/2009 | Kuhnke et al. | |
| 2010/0234335 A1 | 9/2010 | Gravanis et al. | |
| 2014/0094619 A1 | 4/2014 | Runyon et al. | |
| 2014/0275241 A1* | 9/2014 | Covey ................. | C07C 255/47 514/475 |
| 2015/0315230 A1 | 11/2015 | Covey et al. | |

FOREIGN PATENT DOCUMENTS

| | | |
|---|---|---|
| EP | 0104489 A1 | 4/1984 |
| WO | 9640043 A2 | 12/1996 |
| WO | 2008157460 A1 | 12/2008 |
| WO | 2012013816 A1 | 2/2012 |

(Continued)

OTHER PUBLICATIONS

Im et al. (AN:1990:229837; Document No. 112:229837, HCAPLUS, abstract, Molecular Pharmacology (1990), 37(3), 429-34).*

(Continued)

*Primary Examiner* — Sabiha N Qazi

(74) *Attorney, Agent, or Firm* — Armstrong Teasdale LLP

(57) ABSTRACT

The present disclosure is generally directed to neuroactive 19-alkoxy-17-substituted steroids as referenced herein, and pharmaceutically acceptable salts thereof, for use as, for example, an anesthetic, and/or in the treatment of disorders relating to GABA function and activity. The present disclosure is further directed to pharmaceutical compositions comprising such compounds.

7 Claims, No Drawings

(56) References Cited

FOREIGN PATENT DOCUMENTS

| | | |
|---|---|---|
| WO | 2012083090 A2 | 6/2012 |
| WO | 2012116290 A2 | 8/2012 |
| WO | 2013188792 A2 | 12/2013 |
| WO | 2015027227 A1 | 2/2015 |

OTHER PUBLICATIONS

Mok et al. (AN 1991:36197 HCAPLUS, DN 114:36197, abstract of Brain Research (1990), 533(1) 42-45).*
International Search Report for PCT/US2013/076214 dated Jun. 5, 2014.
Cerny et al., Syntheses of 19[0-(carboxymethypoxime] haptens of epipregnanolone and pregnanolone. Steroids, 2006, 71(2), 120-128.
Cerny et al., "Synthetic Approach to 5a-Pregnanolone 19-[0-(Carboxymethyl)Oxime] Derivatives" Collection of Czechoslovak Chemical Communications, 2004, 69(9), 1805-1817.
Wicha et al., "Transformations of steroidal neopentyl systems. II. Migration of acetate from the 3b- to the 19-hydroxyl in a 5 and A/B-trans steroids", Canadian Journal of Chemistry, 1967, 45(7), 707-11.
Hill et al., "34. Photochemische Reaktionen 32. Mitteilung [1] UV.-Bestrahlung von gesattigten and B,y-ungesattigten, homoallylisch konjugierten Steroldaldehyden", Helvetica Chimica Acta, 1966, 49(1), 292-311.
Wicha et al., "Transformations of Steroidal Neopentyl Systems. VII. Mechanism of the Transformation of (19R)-(19)Hydroxy-19-methyl-3-oxo-(5a)-3a-hydroxy-19-methyl-19-oxo(5a)-analogs", Journal of Organic Chemistry, 1973, 38(7), 1280-3.
Wicha et al., "Transformations of Steroidal Neopentyl Systems. Part V. Synthesis and Proof of the Configuration of 19a-Methyl-19S-alcohols," Journal of the Chemical Society (Section) C: Organic, 1969, (6), 947-51.
Wicha et al., "Transformations of Steroidal Neopentyl Systems. IV. Stereochemistry of Products of Reaction of Methyllithium with Steroidal A5-19-aldehydes", Journal of the Chemical Society (Section) C: Organic, 1968, (14), 1740-6.
Caspi et al., "Stereochemistry of 19-hydroxy-19a-methyl steroids", Chemical Communications, 1966, (7), 209-10.
Knox et al., "Steroids. CCLXXVIII. Reductions of 19-substituted androst-4-en-3-ones and related compounds", Journal of Organic Chemistry, 1965, 30(7), 2198-205.
Anderson et al., "Conformationally Constrained Anesthetic Steroids That Modulate GABAA Receptors," Journal of Medicinal Chemistry, Jan. 1, 2000, vol. 43, No. 22, pp. 4118-4125.
Gustafsson et al., "Steroids in Germfree and Conventional Rats. 7. Identification of CI9 and C21 Steroids in Faeces from Conventional Rats," European Journal of Biochemistry, Nov. 1, 1968, vol. 6, No. 2, pp. 248-255.
Gustafsson et al., "Steroid excretion patterns in urine from ovariectomized and adrenalectomized rats," Biochmica ET Biophysica ACTA—Lipids and Lipid Metabolism, Elsevier Science BV, Sep. 7, 1972, vol. 280, No. 1, pp. 182-186.
Gyermek et al., "Steroids, CCCX. 1 Structure-Activity Relationship of Some Steroidal Hypnotic Agents," Journal of Medicinal Chemistry, Jan. 1, 1968, vol. 11, No. 1, pp. 117-125.
Pechet et al, "Metabolism of 19-hydroxycorticosterone. Isolation and characterization of three metabolites," Journal of Biological Chemistry, Jan. 1, 1961, vol. 236, No. 10., pp. PC68-PC69.
Shen et al., "Microbial aromatization of 19-hydroxymethylepidehydroandrosterone acetate by Corynebacterium simplex," Huaxue Xuebao, 1983, vol. 41, No. 5, pp. 473-474.
Wicha et al., "Transformations of steroidal neopentyl systems . VI. Intramolecular Claisen condensation of 19R-acetoxy-19A-methyl-3-ones of the 5.alpha series," Tetrahedron, 1969, vol. 25, No. 17, pp. 3961-3968.
Supplementary European Search Report for EP 13 86 5411, dated Jul. 5, 2016, 16 pages.
Anderson et al. "Anesthetic Activity of Novel Water-Soluble 2β-Morpholinyl Steroids and Their Modulatory Effects at GABA-A Receptors," J. Med. Chem., 1997, vol. 40, pp. 1668-1681.
Bandyopadhyaya et al., "Neurosteroid analogues. 15. A comparative study of the anesthetic and GABAergic actions of alphaxalone, a 16-alphaxalone and their corresponding 17-carbonitrile analogues," Bioorg Med Chem Lett., Nov. 15, 2010, vol. 20, Issue 22, pp. 6680-6684.
Berge et al., J. Pharmaceutical Sciences, 1977, vol. 66, 1-19.
Fajkos et al., "Steroids. XXIII. Synthesis and configuration of the two stereoisomeric 3β-hydroxy-16- acetylandrostanes," Chemicke Listy pro Vedu a Prumysl, vol. 50, pp. 791-799 (1956).
Fesik et al., "Geometric Requirements for Membrance Perturbation and Anesthetic Activity," Molecular Pharmacology, 1985, vol. 27, pp. 624-629.
Green et al., The nonfeminizing enantiomer of 17β-estradiol exerts protective effects in neuronal cultures and a rat mnodel of cerebral ischemia. Endocrinology 2001, vol. 142, pp. 400-406.
Han et al., "Neurosteroid Analogs. 3. The Synthesis and Electrophysiological Evaluation of Benz[e]indene Congeners Df Neuroactive Steroids Having the 5â-Configuration," J. of Med. Chem., 1995, vol. 38(22), pp. 4548-4556.
Hauser et al., "Steroids. CCV. Fragmentations and intramolecular abstractions of tertiary hydrogen atoms by primary oxy radicals with fixed reaction centers," Helv. Chim. Acta, 1964, vol. 47, pp. 1961-1979.
Heard et al., "Steroids. VII. Preparation of androstan-3(β)-ol-7-one from dehydroisoandrosterone," Journal of Biological Chemistry, 1646, vol. 165, pp. 677-685.
Hu et al., Neurosteroid analogues. Part 5. Enantiomers of neuroactive steroids and benz[e]indenes: total synthesis, alectrophysiological effects on GABAA receptor function and anesthetic actions in tadpoles. J. Chem. Soc. Perkin Trans. 1, 1997, pp. 3665-3671.
International Search Report and Written Opinion for PCT/US2012/026542, dated Dec. 12, 2012.
International Search Report and Written Opinion issued for International Application No. PCT/US2014/016405, dated Jul. 16, 2014.
Jiang et al., Neurosteroid analogues. 9. Conformationally constrained pregnanes: structure-activity studies of 13,24-cyclo-18,21-dinorcholane analogues of the GABA modulatory and anesthetic steroids (3α,5α)- and 3α,5α)-3-hydroxypregnan-20-one. J. Med. Chem., 2003, vol. 46, pp. 5334-5348.
Kaji et al., "Synthesis of 3-epi-6, 7- dideoxyxestobergsterol A," Chem. & Pharm. Bulletin, 2000, vol. 48(10), pp. 1480-1483.
Katona et al., Neurosteroid analogues. 12. Potent enhancement of GABA-mediated chloride currents at GABA-A receptors by ent-androgens. Eur. J. Med. Chem. 2008, vol. 43, pp. 107-113.
Morrow, et al., "Characterization of Steroid Interactions with gamma-Aminobutyric Acid Receptor-Gated Chloride Ion Channels: Evidence for Multiple Steroid Recognition Sites," Molecular Pharmacology, 1989, vol. 37, pp. 263-270.
Nilsson et al., Neurosteroid ananlogues. 6. The synthesis and GABAA receptor Pharmacology of enantiomers of dehydroepiandrosterone sulfate, pregnenolone sulfate and (3α,5β)-3-hydroxypregnan-20-one sulfate, J. Med. Chem., 1998, vol. 41, pp. 2604-2613.
Phillips et al., "Structure-Activity Relationships in Steroidal Anaesthetics," Journal of Steroid Biochemistry, 1975, vol. 6, pp. 607-613.
Qian et al., "The efficient and enantiospecific total synthesis of cyclopenta[b]phenanthrenes structurally related to neurosteroids," Adv. Syn. & Cata., 2010, vol. 352 (11-12), pp. 2057-2061.
Qian et al., "Neurosteroid Analogues, 18. Structure-Activity Studies of ent-Steroid Potentiators of γ-Aminobutyric Acid Type a Receptors and Comparison of Their Activities with Those of Alphaxalone and Allopregnanolone," J. of Med. ',Them., 2014, vol. 57(1), pp. 171-190.
Ruzicka et al., "Steroids and sex hormones. CXXXIX. The relation between constitution and odor of steroids. Methylandrostane and allopregnane derivatives," Helvetica Chimica Acta, 1947, vol. 30, pp. 867-878.
Rychnovsky et al., "Synthesis of ent-cholesterol, the unnatural enantiomer," J. of Org. Chem., 1992, vol. 57(9), pp. 2732-2736.

(56) References Cited

OTHER PUBLICATIONS

Santaniello et al., "Reduction of certain steroidal 19-sulfonic esters with metal hydrides," J. of Ster. Biochem., 1976, vol. 7(3), pp. 223-227.

Sarett, L.H., A new method for the preparation of 17(alpha)-hydroxy-20-ketopregnanes. J. Am. Chem. Soc., 1948, 70: 1454-1458.

Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes," J. Med. Chem., 2008, vol. 51, pp. 1309-1318.

Shu et al. Characteristics of concatemeric GABAA receptors containing α4/δ subunits expressed in Xenopus oocytes. British Journal of Pharmacology, 2012, vol. 165, pp. 2228-2243.

Spiegel et al., and Use of Nonaqueous Solvents in Parenteral Products, J. of Pharm. Sciences, 1963, vol. 52, No. 10, pp. 917-927.

Stastna et al., the use of symmetry in enantioselective synthesis: Four pairs of chrysene enantiomers prepared from 19-nortestosterone. Org. Biomol. Chem. 2011, vol. 9, pp. 4685-4694.

Stastna, et al., "Stereoselectivity of sodium borohydride reduction of saturated steroidal ketones utilizing conditions of Luche reduction," Steroids, 2010, vol. 75(10), pp. 721-725.

Stastna et al., Neurosteroid Analogues. 16. A New Explanation for the Lack of Anesthetic Effects in Δ16-Alphaxalone and Identification of a Δ17(20) Analogue with Potent Anesthetic Activity, J. Med. Chem., 2011, vol. 54(11), pp. 3926-3934.

Upasani et al., "3α-Hydroxy-3β-(phenylethynyl-5β-pregnan-20-ones: Synthesis and Pharmacological Activity of Neuroactive Steroids with High Affinity for GABA-A Receptors," J. Med. Chem., 1997, vol. 40, pp. 73-84.

Wu, Kuei-Meng, "A New Classification of Prodrugs: Regulatory Perspectives," Pharmaceuticals, 2009, vol. 2, pp. 77-81.

Non-Final Office Action issued in U.S. Appl. No. 14/132,386 dated Feb. 5, 2016, 16 pages.

Translation of Office Action issued in Chinese Patent Application No. 201380072706.2 dated Apr. 6, 2016, 3 pages.

\* cited by examiner

NEUROACTIVE 19-ALKOXY-17-SUBSTITUTED STEROIDS, PRODRUGS THEREOF, AND METHODS OF TREATMENT USING SAME

CROSS-REFERENCE TO RELATED APPLICATIONS

This application is a U.S. National Phase Patent Application of International Application Serial Number PCT/US2013/076214, filed Dec. 18, 2013, which is incorporated herein in its entirety, and which claims priority benefit of U.S. Provisional Patent Application Ser. No. 61/738,822, filed on Dec. 18, 2012, the entire contents of which is are also incorporated herein by reference.

GOVERNMENT SUPPORT

The claimed subject matter was developed with Government support under NIH Grant #GM47969, awarded by the National Institute of Health. Accordingly, the Government has certain rights in the claimed subject matter.

BACKGROUND OF THE DISCLOSURE

The present disclosure is generally directed to novel compounds having utility as an anesthetic and/or in the treatment of disorders relating to GABA function and activity. More specifically, the present disclosure is directed to steroids having a 19-alkoxy-17-substituted tetracyclic structure that are neuroactive and suitable for use as an anesthetic, as well as pharmaceutically acceptable salts and prodrugs thereof, and pharmaceutical compositions containing them.

Gamma-aminobutyric acid (GABA) is the major inhibitory neurotransmitter of the central nervous system. GABA activates two types of receptors, the inotropic $GABA_A$ and the metabotropic $GABA_B$ receptor. Activation of the $GABA_B$ receptor by GABA causes hyperpolarization and a resultant inhibition of neurotransmitter release. The $GABA_A$ receptor subtype regulates neuronal excitability and rapid mood changes, such as anxiety, panic, and stress response. $GABA_A$ receptors are chloride ion channels; as a result, activation of the receptor induces increased inward chloride ion flux, resulting in membrane hyperpolarization and neuronal inhibition. Drugs that stimulate $GABA_A$ receptors, such as benzodiazepines and barbiturates, have anticonvulsive effects (by reducing neuronal excitability and raising the seizure threshold), as well as anxiolytic and anesthetic effects.

The effect of certain steroids on $GABA_A$ receptors has been well-established. As a result, researchers continue to pursue the discovery and synthesis of neuroactive steroids that may act as anesthetics and/or that may serve to provide treatment for disorders related to GABA function. For example, it is now widely accepted that the intravenous anesthetic alphaxalone (Compound A, below) causes general anesthesia in humans because it allosterically increases chloride currents mediated by GABA acting at $GABA_A$ receptors in the brain. However, the various structural features that enable this compound to function in the way it does have, to-date, not been fully understood. For example, in contrast to alphaxalone, $\Delta^{16}$-alphaxalone (Compound B, below), has been observed to have greatly diminished allosteric activity at $GABA_A$ receptors and is not used as an intravenous general anesthetic in humans.

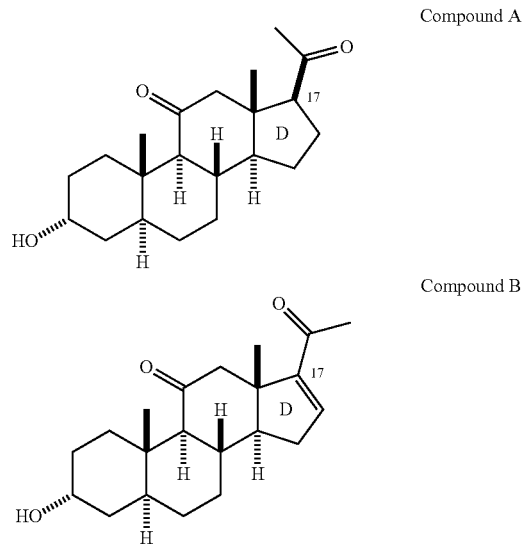

The difference in performance of these two compounds, which some have attributed to the presence of the carbon-carbon double bond in the D-ring, has attracted the attention of many researchers. In fact, recently, it was determined that the effect this double bond has on anesthetic activity may depend on the group attached at C-17 on the D-ring. (See Bandyopadhyaya, A. K., et al., "Neurosteroid analogues. 15. A comparative study of the anesthetic and GABAergic actions of alphaxalone, $\Delta^{16}$-alphaxalone and their corresponding 17-carbonitrile analogues. Bioorg. Med. Chem. Lett., 20: 6680-4 (2010).)

In addition to anesthetic properties, neuroactive steroids may be used to treat disorders related to GABA function. For example, neuroactive steroids, such as progesterone, may be used as sedative-hypnotics, exhibiting benzodiazepine-like actions, inducing reduced sleep latency and increased non-REM sleep with only small changes in slow wave and REM sleep. Further, drugs that enhance GABA responses are often used to treat anxiety in humans. Thus, it might be expected that GABA-potentiating steroids would exhibit anxiolytic effects. Neuroactive steroids may also be used to treat depression, given that accumulating evidence suggests that patients with major depression have decreased levels of GABAergic neurosteroids and that certain treatments for depression alter levels of these steroids. Although GABA is not typically thought to play a critical role in the biology of depression, there is evidence that low GABAergic activity may predispose one to mood disorders. Finally, inhibition of NMDA receptors and enhancement of GABAA receptors appear to play important roles in mediating the acute effects of ethanol in the nervous system, while related studies suggest that GABAergic neurosteroids may be involved in some of the pharmacological effects of ethanol and that neuroactive steroids may be useful in treating ethanol withdrawal.

In view of the foregoing, it is clear that there are a number of potentially advantageous uses for neurosteroids. As a result, there is a continuing need for the further synthesis and understanding of new neuroactive steroids, particularly those having utility as an anesthetic and/or in the treatment of a disorder relating to GABA function and activity.

SUMMARY OF THE DISCLOSURE

In one aspect, the present disclosure is directed to a compound having a structure of Formula (I):

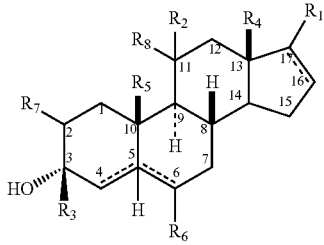

(I)

or a pharmaceutically acceptable salt thereof;
wherein:

R1 is selected from (C1-C4 alkyl)-O, spirooxirane, cyano, =O, nitro, (C1-C4 alkyl)C(O), and HO(C1-C4 alkyl)C(O), with R1 preferably being in the beta position when other than =O, and/or in one or more preferred embodiments C1-C4 alkyl being methyl, R1 therefore being is selected from methoxy, spirooxirane, cyano, =O, nitro, CH3C(O)— and OHCH2C(O)—;

R2 is =O, H, or ORa, where Ra is selected from H, optionally substituted C1-C4 alkyl, or optionally substituted aryl, with the proviso that when R2 is =O, R8 is not present;

R3 is H, optionally substituted C1-C4 alkyl, optionally substituted C2-C4 alkenyl, optionally substituted C2-C4 alkynyl, or optionally substituted aryl;

R4 is independently selected from H and unsubstituted C1-C4 alkyl;

R5 is substituted C1-C4 alkyl, optionally substituted C2-C4 alkenyl, or optionally substituted C2-C4 alkynyl (and in particular is alkoxy-substituted methyl, or even more particular is —CH2-ORb, where Rb is C1-C4 alkyl, or even still more particularly is —CH2-OCH3);

R6 is H, optionally substituted C1-C4 alkyl, or optionally substituted C1-C4 alkoxy;

R7 is H, optionally substituted C1-C4 alkoxy, or an optionally substituted morpholinyl ring;

R8, when present, is H or optionally substituted C1-C4 alkyl;

- - - denotes an optional, additional C—C bond, resulting in either a C=C bond between C4-O5 or C5-C6, with the proviso that when present, the R5-H substituent is not present; and,

- - - denotes an optional, additional C—C bond, resulting in a C=C bond between C16-C17, with the proviso that when present, the R1 is not =O.

The present disclosure is further directed to a pharmaceutically acceptable salt of the noted compounds, or alternatively to prodrugs thereof. In one particular embodiment, the present disclosure is directed to a compound having a structure of Formula (II):

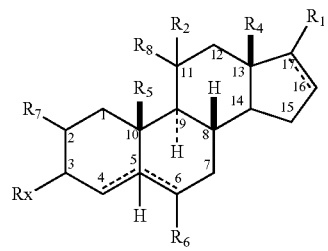

(II)

or a pharmaceutically acceptable salt thereof;
wherein:

R1 is selected from (C1-C4 alkyl)-O, spirooxirane, cyano, =O, nitro, (C1-C4 alkyl)C(O), and HO(C1-C4 alkyl)C(O), with R1 preferably being in the beta position when other than =O, and/or in one or more preferred embodiments C1-C4 alkyl being methyl, R1 therefore being is selected from methoxy, spirooxirane, cyano, =O, nitro, CH3C(O)— and OHCH2C(O)—;

R2 is =O, H, or ORa, where Ra is selected from H, optionally substituted C1-C4 alkyl, or optionally substituted aryl, with the proviso that when R2 is =O, R8 is not present;

Rx is =O or ORd, where Rd is H or C(O)Re, where Re is optionally substituted C1-C22 alkyl or optionally substituted C2-C22 alkenyl, with the proviso that when Rx is OH, it is in the beta configuration;

R4 is independently selected from H and unsubstituted C1-C4 alkyl;

R5 is substituted C1-C4 alkyl, optionally substituted C2-C4 alkenyl, or optionally substituted C2-C4 alkynyl (and in particular is alkoxy-substituted methyl, or even more particular is —CH2-ORb, where Rb is C1-C4 alkyl, or even still more particularly is —CH2-OCH3);

R6 is H, optionally substituted C1-C4 alkyl, or optionally substituted C1-C4 alkoxy;

R7 is H, optionally substituted C1-C4 alkoxy, or an optionally substituted morpholinyl ring;

R8, when present, is H or optionally substituted C1-C4 alkyl;

- - - denotes an optional, additional C—C bond, resulting in either a C=C bond between C4-C5 or C5-C6, with the proviso that when present, the C5-H substituent is not present; and,

- - - denotes an optional, additional C—C bond, resulting in a C=C bond between C16-C17, with the proviso that when present, the R1 is not =O, provided that the compound does not have one of the following structures:

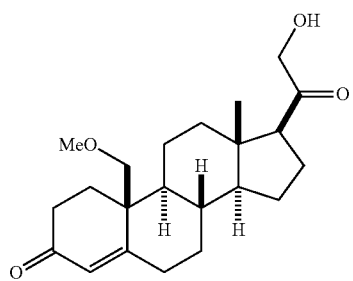

-continued

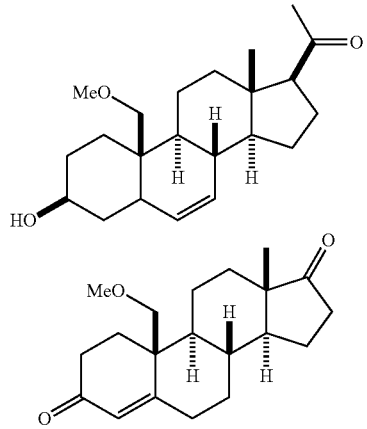

or alternatively provided that: (i) when $R_x$ is =O, a C=C bond is present between $C_4$-$C_5$, and $R_5$ is $CH_2OCH_3$, then $R_1$ is selected from methoxy, spirooxirane, cyano, nitro, and $CH_3C(O)$—; and/or (ii) when $R_x$ is beta-OH, a C=C bond is present between $C_5$-$C_6$, and $R_5$ is $CH_2OCH_3$, then $R_1$ is selected from methoxy, spirooxirane, cyano, nitro, and $HOCH_2C(O)$—.

The present disclosure is still further directed to a pharmaceutical composition comprising a therapeutically effective amount of one or more of the above-noted steroids, or prodrugs, or pharmaceutically acceptable salts thereof, and optionally a pharmaceutically acceptable carrier. The present disclosure also provides kits comprising steroids, salts thereof, pro-drugs thereof, and/or pharmaceutical compositions thereof.

The present disclosure further provides methods of inducing anesthesia in a subject in need thereof, the method comprising administering to the subject a therapeutically effective amount of one or more of the above-noted steroids, or prodrugs, or pharmaceutically acceptable salts thereof, or a pharmaceutical composition thereof.

The present disclosure further provides methods of treating disorders related to GABA function in a subject in need thereof, the method comprising administering to the subject a therapeutically effective amount of one or more of the above-noted steroids, or prodrugs, or pharmaceutically acceptable salts thereof, or a pharmaceutical composition thereof. In certain embodiments, the disorder is selected from the group consisting of insomnia, mood disorders, convulsive disorders, anxiety, or symptoms of ethanol withdrawal.

DETAILED DESCRIPTION OF CERTAIN EMBODIMENTS

In accordance with the present disclosure, it has been discovered that compounds having certain 17-substituted steroid structures, more specifically certain 19-alkoxy-17-substituted steroid structures, and even more specifically certain 19-methoxy-17-substituted steroid structures, are neuroactive and are also suitable for use as anesthetics and in the treatment of disorders associated with GABA function, as well as pharmaceutically acceptable salts and pro-drugs thereof. The compounds may be used, for example, as an effective continuous infusion sedative for non-surgical procedures (e.g., colonoscopy). The compounds also offer advantages over anesthetics known in the art, such as a lower likelihood for bacterial contamination, as well as an improved relationship with solubilizing agents.

1. Steroid Structure

Generally speaking, the steroid of the present disclosure has a tetracyclic, fused ring structure, such as a cyclopenta[α]phenanthrene ring system (an embodiment of which is illustrated and discussed in greater detail below), wherein the $C_3$-position of the A ring has a hydroxyl substituent in the α-position, and the $C_{17}$-position of the D ring has a substituent attached thereto selected from the group consisting of methoxy, spirooxirane, cyano, =O, nitro, $CH_3C(O)$—, and $HOCH_2C(O)$— (with $R_1$ preferably being in the beta position when other than =O).

More particularly, however, the present disclosure is directed, in certain embodiments, to a steroid having the structure of Formula (I):

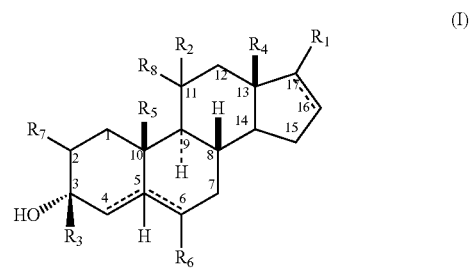

(I)

or a pharmaceutically acceptable salt thereof;
wherein:
$R_1$ is selected from ($C_1$-$C_4$ alkyl)-O (e.g., methoxy, ethoxy, propoxy, butoxy), spirooxirane, cyano, =O, nitro, ($C_1$-$C_4$ alkyl)C(O) (e.g., $CH_3C(O)$, $CH_3CH_2C(O)$, $CH_3CH_2CH_2C(O)$, $CH_3CH_2CH_2CH_2C(O)$), and HO($C_1$-$C_4$ alkyl)C (O) (e.g., $HOCH_2C(O)$, $HOCH_2CH_2C(O)$, $HOCH_2CH_2CH_2C(O)$, $HOCH_2CH_2CH_2CH_2C(O)$), with $R_1$ preferably being in the beta position when other than =O, and/or in one or more preferred embodiments $C_1$-$C_4$ alkyl being methyl, $R_1$ therefore being is selected from methoxy, spirooxirane, cyano, =O, nitro, $CH_3C(O)$— and $OHCH_2C(O)$—;
$R_2$ is =O, H, or ORa, where Ra is selected from H, optionally substituted C1-C4 alkyl, or optionally substituted aryl, with the proviso that when R2 is =O, R8 is not present;
R3 is H, optionally substituted C1-C4 alkyl, optionally substituted C2-C4 alkenyl, optionally substituted C2-C4 alkynyl, or optionally substituted aryl;
R4 is independently selected from H and unsubstituted C1-C4 alkyl;
R5 is substituted C1-C4 alkyl, optionally substituted C2-C4 alkenyl, or optionally substituted C2-C4 alkynyl (and in particular is alkoxy-substituted methyl, or even more particular is —$CH_2$—$OR_b$, where $R_b$ is $C_1$-$C_4$ alkyl, or even still more particularly is —$CH_2$—$OCH_3$);
$R_6$ is H, optionally substituted $C_1$-$C_4$ alkyl, or optionally substituted $C_1$-$C_4$ alkoxy;
$R_7$ is H, optionally substituted C1-C4 alkoxy, or an optionally substituted morpholinyl ring;
R8, when present, is H or optionally substituted C1-C4 alkyl;
- - - denotes an optional, additional C—C bond, resulting in either a C=C bond between C4-C5 or C5-C6, with the proviso that when present, the R5-H substituent is not present; and,

- - - denotes an optional, additional C—C bond, resulting in a C=C bond between C16-C17, with the proviso that when present, the R1 is not =O.

As generally defined above, $R_1$ is selected from ($C_1$-$C_4$ alkyl)-O, spirooxirane, cyano, =O, nitro, ($C_1$-$C_4$ alkyl)C(O), and HO($C_1$-$C_4$ alkyl)C(O). In certain embodiments, $R_1$ is preferably in the beta position (when other than =O, or when a C=C is not present between $C_{16}$-$C_{17}$). In certain embodiments, $R_1$ is selected from ($C_1$-$C_4$ alkyl)-O (e.g., methoxy, ethoxy, propoxy, butoxy), spirooxirane, cyano, =O, nitro, ($C_1$-$C_4$ alkyl)C(O) (e.g., $CH_3C(O)$, $CH_3CH_2C(O)$, $CH_3CH_2$ $CH_2C(O)$, $CH_3CH_2$ $CH_2$ $CH_2C(O)$), and HO($C_1$-$C_4$ alkyl)C(O) (e.g., $HOCH_2C(O)$, $HOCH_2CH_2C(O)$, $HOCH_2CH_2$ $CH_2C(O)$, $HOCH_2CH_2$ $CH_2$ $CH_2C(O)$). In certain embodiments, $C_1$-$C_4$ alkyl is methyl, $R_1$ therefore being is selected from methoxy, spirooxirane, cyano, =O, nitro, $CH_3C(O)$— and $OHCH_2C(O)$—.

As generally defined above, $R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present. In certain embodiments, $R_2$ is =O and $R_8$ is not present. In certain embodiments, $R_2$ is H. In certain embodiments, $R_2$ is $OR_a$. In certain embodiments, $R_2$ is $OR_a$ and $R_a$ is optionally substituted $C_1$, $C_2$, $C_3$, or $C_4$ alkyl (e.g., methyl, ethyl), optionally substituted benzyl, or $C_1$, $C_2$, $C_3$, or $C_4$ alkyl substituted with O-aryl, such as O-benzyl. In certain embodiments, $R_2$ is $OR_a$ and $R_a$ is optionally substituted aryl. In certain embodiments, $R_2$ is $OR_a$ and $R_a$ is H.

As generally defined above, $R_3$ is H, optionally substituted $C_1$-$C_4$ alkyl, optionally substituted $C_2$-$C_4$ alkenyl, optionally substituted $C_2$-$C_4$ alkynyl, or optionally substituted aryl. In certain embodiments, $R_3$ is H. In certain embodiments, $R_3$ is optionally substituted $C_1$, $C_2$, $C_3$ or C4 alkyl (e.g., methyl, ethyl, trifluoromethyl, difluoromethyl). In certain embodiments, $R_3$ is methyl. In certain embodiments, $R_3$ is trifluoromethyl. In certain embodiments, $R_3$ is optionally substituted $C_2$, $C_3$ or $C_4$ alkenyl (e.g., optionally substituted allyl). In certain embodiments, $R_3$ is optionally substituted $C_2$, $C_3$, or $C_4$ alkynyl (e.g., optionally substituted acetylene or optionally substituted propargyl). In certain embodiments, $R_3$ is optionally substituted aryl (e.g., optionally substituted phenyl, such as phenyl substituted with OH, methyl, or $COR_c$, where $R_c$ is optionally substituted $C_1$-$C_{22}$ alkyl or optionally substituted $C_2$-$C_{22}$ alkenyl, including for example optionally substituted $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl or $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkenyl).

As generally defined above, $R_4$ is H or unsubstituted $C_1$-$C_4$ alkyl. In certain embodiments, $R_4$ is H. In certain embodiments, $R_4$ is unsubstituted $C_1$, $C_2$, $C_3$ or $C_4$ alkyl (e.g., methyl, ethyl, n-propyl, isopropyl, or n-butyl).

As generally defined above, $R_5$ is substituted $C_1$-$C_4$ alkyl, optionally substituted $C_2$-$C_4$ alkenyl, or optionally substituted $C_2$-$C_4$ alkynyl. In certain embodiments, $R_5$ is substituted $C_1$-$C_4$ alkyl, and in particular is alkoxy-substituted $C_1$-$C_4$ alkyl. In other particular embodiments, $R_5$ is substituted methyl, and more particularly is alkoxy-substituted methyl (or even more particularly is —$CH_2$—$OR_b$, where $R_b$ is $C_1$-$C_4$ alkyl, or even still more particularly is —$CH_2$—$OCH_3$). In other embodiments, $R_5$ is optionally substituted $C_2$-$C_4$ alkenyl. In other embodiments, $R_5$ is optionally substituted $C_2$-$C_4$ alkynyl.

As generally defined above, $R_6$ is H, optionally substituted $C_1$-$C_4$ alkyl, or optionally substituted $C_1$-$C_4$ alkoxy. In certain embodiments, $R_6$ is H. In certain embodiments, $R_6$ is optionally substituted $C_1$, $C_2$, $C_3$, or $C_4$ alkyl (e.g., methyl). In certain embodiments, $R_6$ is optionally substituted $C_1$, $C_2$, $C_3$ or $C_4$ alkoxy (e.g., methoxy, ethoxy, n-propyloxy, iso-propyloxy, or n-butoxy). In certain embodiments, when $R_6$ is a non-hydrogen group, $R_6$ is in the alpha (down) position. In certain preferred embodiments, however, when $R_6$ is a non-hydrogen group, $R_6$ is in the beta (up) position.

As generally defined above, $R_7$ is H, optionally substituted $C_1$-$C_4$ alkoxy, or an optionally substituted morpholinyl ring. In certain embodiments, $R_7$ is H. In certain embodiments, $R_7$ is optionally substituted $C_1$, $C_2$, $C_3$ or $C_4$ alkoxy (e.g., methoxy, ethoxy, n-propyloxy, isopropyloxy, or n-butoxy). In certain embodiments, $R_7$ is an optionally substituted morpholinyl ring. In certain embodiments, when $R_7$ is a non-hydrogen group, $R_7$ is in the alpha (down) position. In certain preferred embodiments, however, when $R_7$ is a non-hydrogen group, $R_7$ is in the beta (up) position.

As generally defined above, $R_8$, when present, is H or optionally substituted $C_1$-$C_4$ alkyl. In certain embodiments, $R_8$ is H. In certain embodiments, $R_8$ is $C_1$, $C_2$, $C_3$ or $C_4$ optionally substituted alkyl (e.g., methyl). In certain embodiments, when $R_8$ is optionally substituted $C_1$-$C_4$ alkyl, $R_8$ is in the alpha (down) position. In certain embodiments, when $R_8$ is optionally substituted $C_1$-$C_4$ alkyl, $R_8$ is in the beta (up) position.

In certain embodiments, R2 and R8 are both H. In certain embodiments, R2 is ORa and R8 is H.

As generally defined above, - - - denotes an optional, additional C—C bond, resulting in either a C=C bond between C4-C5 or C5-C6, with the proviso that when present, the C5-H substituent is not present. In certain embodiments, the additional C—C bond is absent, and the hydrogen at C5 is in the alpha or beta position. In certain embodiments, the additional C—C bond is absent, and the hydrogen at C5 is in the alpha (down) position. In certain embodiments, the additional C—C bond is absent, and the hydrogen at C5 is in the beta (up) position. In certain embodiments, - - - denotes an additional C—C bond, resulting in a C=C bond between C4-05. In certain embodiments, - - - denotes an additional C—C bond, resulting in a C=C bond between C5-C6.

As generally defined above, - - - denotes an optional, additional C—C bond, resulting in a C=C bond, between C16-C17, with the proviso that when present, the R1 is other than =O. In certain embodiments, the additional C—C bond is absent (i.e., there is not C=C bond), and therefore R1 may be in the alpha or beta position. In certain embodiments, the additional C—C bond is absent, and the $R_1$ is in the alpha (down) position. In certain embodiments, the additional C—C bond is absent, and the $R_1$ is in the beta (up) position.

It is to be noted that the present disclosure contemplates and is intended to encompass all of the various combinations and permutations (i.e., combinations of substituent options, locations and stereochemical configurations) possible here.

For example, in various embodiments, compounds of the present disclosure may be selected from among those encompassed by the structure of Formula (I), wherein $R_2$ is =O; alternatively, $R_2$ may be H and $R_8$ is H (e.g., $C_{11}$ thus having two hydrogen atoms bound thereto as substituents). In certain embodiments, $R_2$ may be $OR_a$, wherein $R_a$ is methyl, optionally substituted benzyl, or $C_1$-$C_4$ alkyl substituted with O-aryl, such as O-benzyl. In certain embodiments, $R_3$ may be H, methyl, trifluoromethyl, or substituted aryl (e.g., substituted phenyl, which in turn may be optionally substituted such as, for example, with OH, methyl, or $COR_c$, where $R_c = C_1-C_4$ alkyl); further, when $R_3$ is something other than H, $R_3$ is preferably in the β-position. In certain embodiments, each of $R_4$ and $R_6$ are independently selected from H and methyl, $R_5$ being in the β-configuration and $R_6$ optionally being in the α-configuration or β-configuration (e.g., when $R_6$ is methyl), which the β-configuration being preferred. In certain embodiments, $R_7$ is selected from H, methoxy, ethoxy, and an optionally substituted morpholinyl ring; further, when $R_7$ is something other than H, $R_7$ is preferably in the β-position. In certain embodiments, $R_8$, when present, is selected from H or optionally substituted $C_1-C_4$ alkyl. In certain embodiments, $R_8$ is methyl (e.g., methyl in the alpha-configuration).

In certain embodiments, the $C_5$—H is in the alpha configuration and the $R_5$ is, for example, a substituted methyl group (e.g., alkoxy-substituted methyl, or in particular a methoxy-substituted methyl) in the beta configuration. In certain embodiments, the C5-H is in the beta configuration and $R_5$ is, for example, a substituted methyl (e.g., a methoxy-substituted methyl) group in the beta configuration. In certain embodiments, $R_6$ is H. In certain embodiments, $R_4$ is methyl. In certain embodiments, $R_2$ is =O or methoxy.

Accordingly, as noted, the steroid of Formula (I) may encompass a number of various structures in accordance with the present disclosure.

In certain embodiments, wherein $R_1$ is as defined above, $R_3$ is in the beta position, $R_4$ is methyl, $R_5$ is substituted methyl in the beta position, and $R_6$ is H, provided is a compound of Formula (I-a):

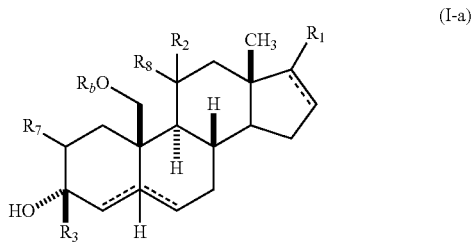

(I-a)

or a pharmaceutically acceptable salt thereof, wherein - - - , $R_2$, $R_3$, $R_7$ and $R_8$ are as defined herein, and further wherein $R_b$ is optionally substituted $C_1-C_4$ alkyl. In certain embodiments, each instance of - - - between $C_5-C_6$ and $C_6-C_7$ is absent and $C_5$—H is in the alpha position. In certain embodiments, each instance of - - - between $C_5-C_6$ and $C_6-C_7$ is absent and $C_5$—H is in the beta position. In certain embodiments, each instance of - - - between $C_{16}-C_{17}$ is absent and $R_1$ is in the beta position.

In certain embodiments of Formula (I), wherein $R_2$ is =O and $R_8$ is absent, provided is a compound of Formula (I-b):

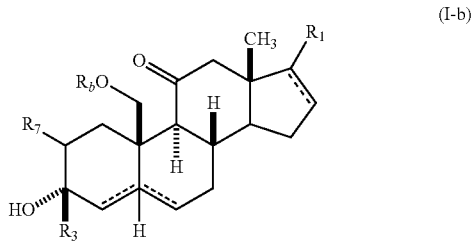

(I-b)

or a pharmaceutically acceptable salt thereof, wherein - - - , $R_3$ and $R_7$ are as defined herein, and further wherein $R_b$ is optionally substituted $C_1-C_4$ alkyl. In certain embodiments, each instance of - - - between $C_5-C_6$ and $C_6-C_7$ is absent and $C_5$—H is in the alpha position. In certain embodiments, each instance of - - - between $C_5-C_6$ and $C_6-C_7$ is absent and $C_5$—H is in the beta position. In certain embodiments, each instance of - - - between $C_{16}-C_{17}$ is absent and $R_1$ is in the beta position.

In certain embodiments of Formula (I), wherein $R_2$ and $R_8$ are H, provided is a compound of Formula (I-c):

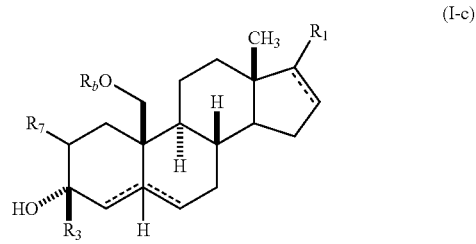

(I-c)

or a pharmaceutically acceptable salt thereof, wherein - - - , $R_2$, $R_3$, and $R_7$ are as defined herein, and further wherein $R_b$ is optionally substituted $C_1-C_4$ alkyl. In certain embodiments, each instance of - - - between $C_5-C_6$ and $C_6-C_7$ is absent and $C_5$—H is in the alpha position. In certain embodiments, each instance of - - - between $C_5-C_6$ and $C_6-C_7$ is absent and $C_5$—H is in the beta position. In certain embodiments, each instance of - - - between $C_{16}-C_{17}$ is absent and $R_1$ is in the beta position.

In certain embodiments of Formula (I), wherein $R_2$ is $OR_a$ and $R_8$ is H, provided is a compound of Formula (I-d):

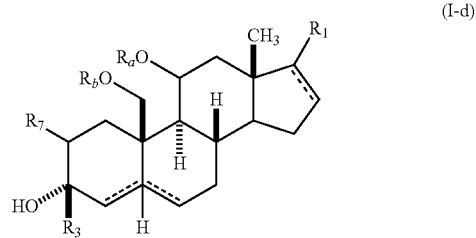

(I-d)

or a pharmaceutically acceptable salt thereof, wherein - - - , $R_3$, $R_7$, and $R_a$ are as defined herein, and further wherein $R_b$ is optionally substituted $C_1-C_4$ alkyl. In certain embodiments, each instance of - - - between $C_5-C_6$ and $C_6-C_7$ is absent and $C_5$—H is in the alpha position. In certain embodiments, each instance of - - - between $C_5-C_6$ and $C_6-C_7$ is absent and $C_5$—H is in the beta position. In certain embodiments, each instance of - - - between $C_{16}-C_{17}$ is absent and $R_1$ is in the beta position.

In certain embodiments of Formula (I), wherein $R_7$ is H, provided is a compound of Formula (I-e):

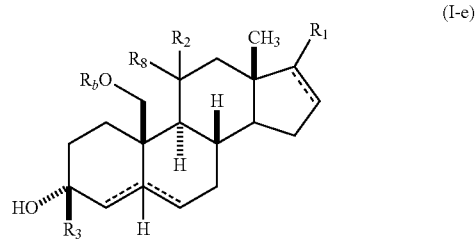

(I-e)

or a pharmaceutically acceptable salt thereof, wherein - - - , $R_2$, $R_3$, and $R_8$ are as defined herein, and further wherein $R_b$ is optionally substituted $C_1$-$C_4$ alkyl. In certain embodiments, each instance of - - - between $C_5$-$C_6$ and $C_6$-$C_7$ is absent and $C_5$—H is in the alpha position. In certain embodiments, each instance of - - - between $C_5$-$C_6$ and $C_6$-$C_7$ is absent and $C_5$—H is in the beta position. In certain embodiments, each instance of - - - between $C_{16}$-$C_{17}$ is absent and $R_1$ is in the beta position.

In certain embodiments of Formula (I), wherein each instance of - - - is absent and $C_5$—H is in the alpha position, provided is a compound of Formula (I-f):

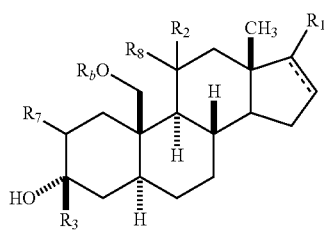

(I-f)

or a pharmaceutically acceptable salt thereof, wherein $R_2$, $R_3$, $R_7$ and $R_8$ are as defined herein, and further wherein $R_b$ is optionally substituted $C_1$-$C_4$ alkyl. In certain embodiments, each instance of - - - between $C_{16}$-$C_{17}$ is absent and $R_1$ is in the beta position.

In certain embodiments of Formula (I), wherein $R_7$ is H, provided is a compound of Formula (I-g):

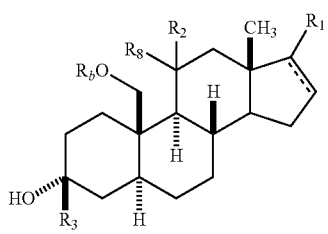

(I-g)

or a pharmaceutically acceptable salt thereof, wherein $R_2$, $R_3$, and $R_8$ are as defined herein, and further wherein $R_b$ is optionally substituted $C_1$-$C_4$ alkyl. In certain embodiments, each instance of - - - between $C_{16}$-$C_{17}$ is absent and $R_1$ is in the beta position.

In certain embodiments of Formula (I), wherein $R_2$ is =O, provided is a compound of Formula (I-h):

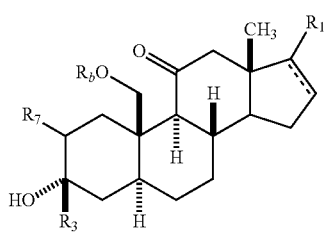

(I-h)

or a pharmaceutically acceptable salt thereof, wherein $R_3$ and $R_7$ are as defined herein, and further wherein $R_b$ is optionally substituted $C_1$-$C_4$ alkyl. In certain embodiments, each instance of - - - between $C_{16}$-$C_{17}$ is absent and $R_1$ is in the beta position.

In certain embodiments of Formula (I), wherein $R_2$ is $OR_a$, provided is a compound of Formula (I-i):

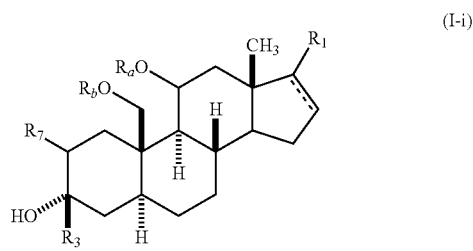

(I-i)

or a pharmaceutically acceptable salt thereof, wherein $R_a$, $R_3$, and $R_7$ are as defined herein, and further wherein $R_b$ is optionally substituted $C_1$-$C_4$ alkyl. In certain embodiments, each instance of - - - between $C_{16}$-$C_{17}$ is absent and $R_1$ is in the beta position.

In certain embodiments of Formula (I), wherein - - - represents an additional C—C bond, resulting in a C=C bond between $C_4$-$C_5$ provided is a compound of Formula (I-j):

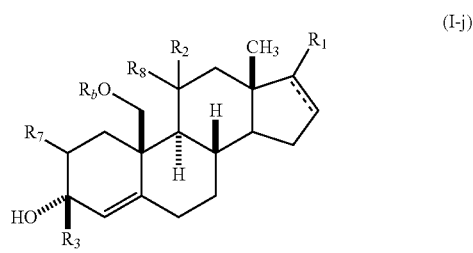

(I-j)

or a pharmaceutically acceptable salt thereof, wherein $R_3$, $R_2$, $R_7$ and $R_8$ are as defined herein, and further wherein $R_b$ is optionally substituted $C_1$-$C_4$ alkyl. In certain embodiments, each instance of - - - between $C_{16}$-$C_{17}$ is absent and $R_1$ is in the beta position.

In certain embodiments of Formula (I), wherein - - - represents an additional C—C bond, resulting in a C=C bond between $C_5$-$C_6$ provided is a compound of Formula (I-k):

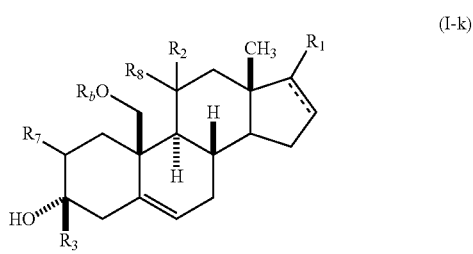

(I-k)

or a pharmaceutically acceptable salt thereof, wherein $R_3$, $R_2$, $R_7$ and $R_8$ are as defined herein, and further wherein $R_b$ is optionally substituted $C_1$-$C_4$ alkyl. In certain embodiments, each instance of - - - between $C_{16}$-$C_{17}$ is absent and $R_1$ is in the beta position.

It is to be noted that, in one or more of the preferred embodiments detailed above, $R_1$ may, in particular, be selected from methoxy (or more generally lower alkoxy, e.g., —O—($C_1$-$C_4$)), or alternatively selected from $CH_3C(O)$— or $HOCH_2C(O)$— (or more generally substituted or unsubstituted lower alkyl-carbonyl, e.g., ($C_1$-$C_4$)C(O)—, wherein one or more of the carbon atoms is optionally substituted, such as for example by a hydroxyl group). Alternatively, $R_1$ may be selected from nitro or cyano, with an optional C=C being present between $C_{16}$-$C_{17}$. In yet another alternative embodiment, $C_{17}$ may be a carbonyl carbon (i.e., $R_1$ is =O), or it may be part of an oxirane ring fused with the D-ring (i.e., $R_1$ being a spirooxirane substituent, wherein $C_{17}$ is the carbon atom common to both rings).

Exemplary compounds of Formula (I) include, but are not limited to, the following:

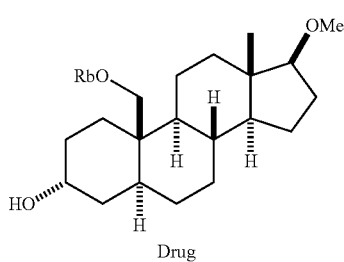
MQ-89

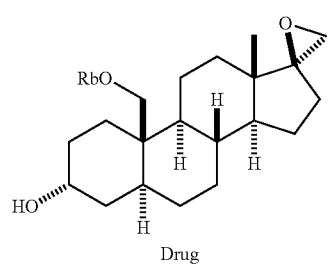
MQ-90

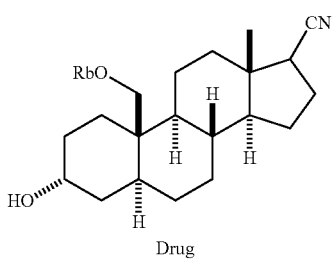
MQ-91

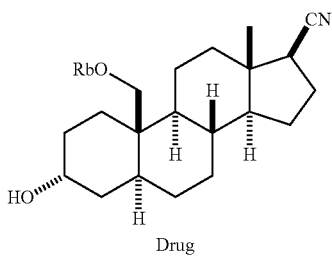
MQ-92

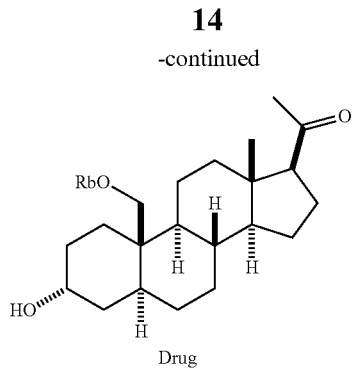
MQ-93

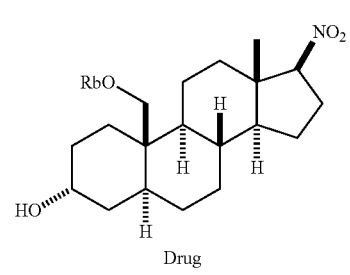
MQ-97

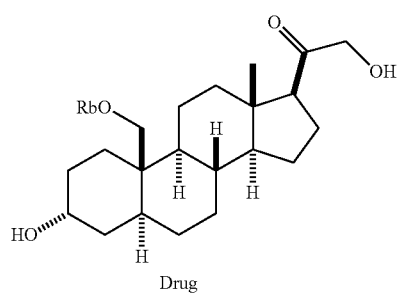
MQ-98

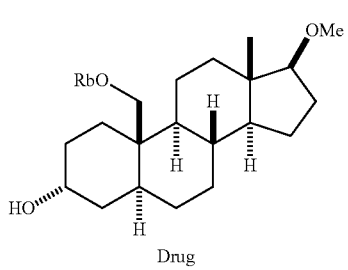
MQ-101

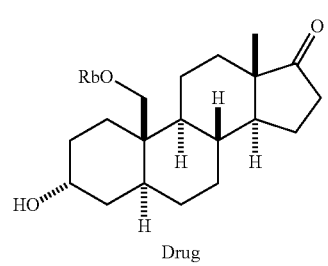
KK-125 and pharmaceutically acceptable salts thereof, wherein in one preferred embodiment $R_b$ is $CH_3$.

In certain embodiments, the steroid of Formula (I) is selected from the group consisting of:

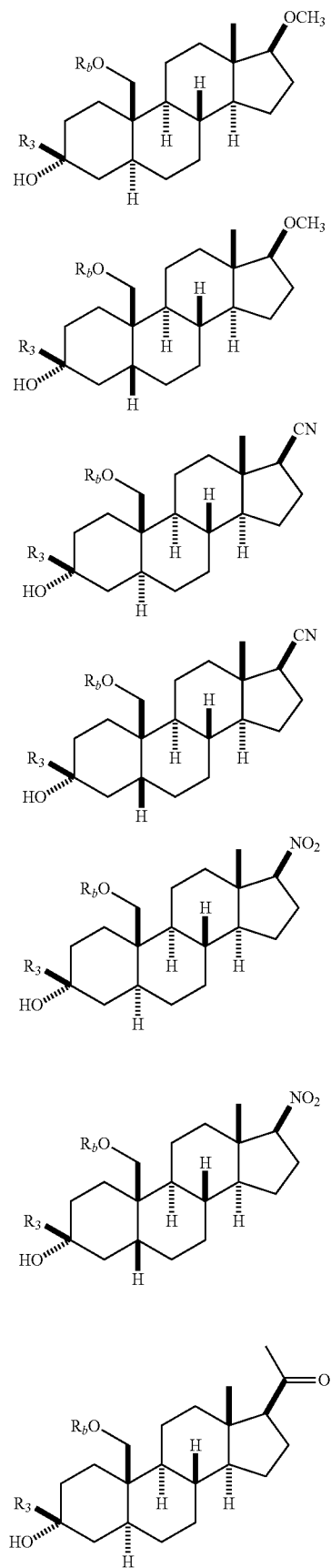

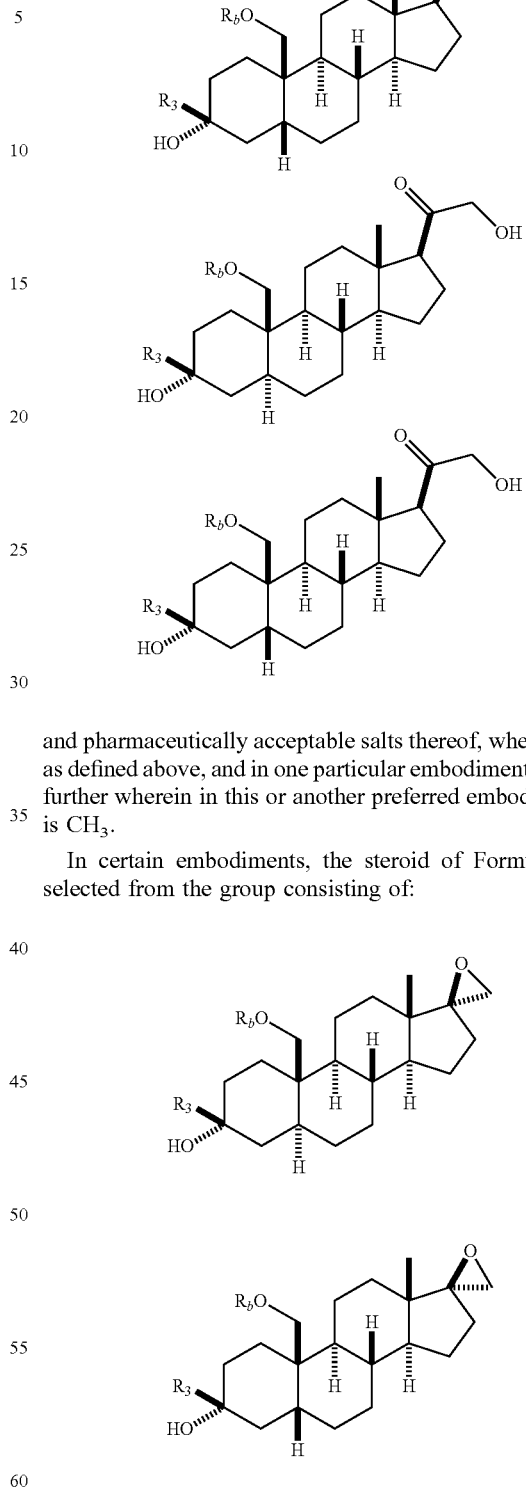

and pharmaceutically acceptable salts thereof, wherein $R_3$ is as defined above, and in one particular embodiment is H, and further wherein in this or another preferred embodiment $R_b$ is $CH_3$.

In certain embodiments, the steroid of Formula (I) is selected from the group consisting of:

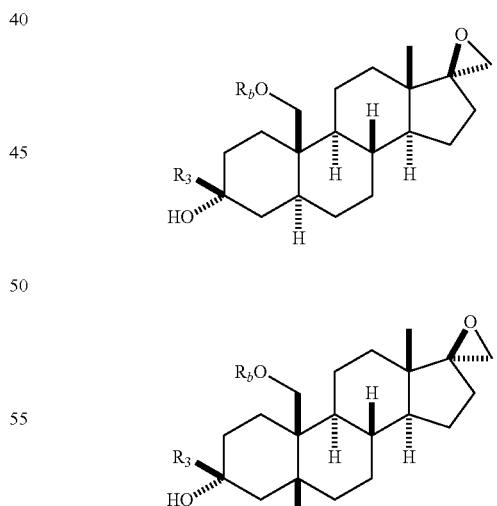

and pharmaceutically acceptable salts thereof, wherein $R_3$ is as defined above, and in one particular embodiment is H, and further wherein in this or another preferred embodiment $R_b$ is $CH_3$.

In certain embodiments, the steroid of Formula (I) is selected from the group consisting of:

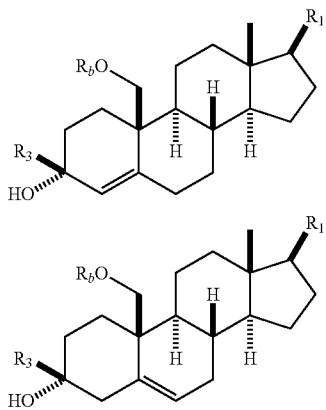

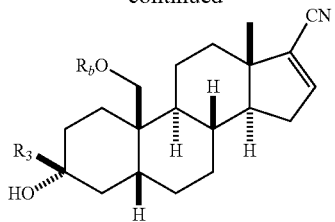

and a pharmaceutically acceptable salt thereof, wherein $R_3$ and/or $R_1$ are as defined above, and in one particular embodiment $R_3$ is H and $R_1$ is methoxy, and further wherein in these or other preferred embodiments $R_b$ is $CH_3$.

In certain embodiments, the steroid of Formula (I) is selected from the group consisting of:

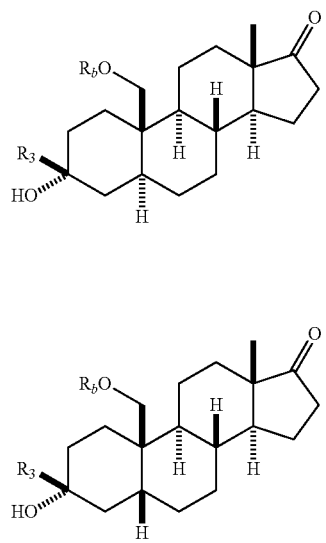

and a pharmaceutically acceptable salt thereof, wherein $R_3$ is as defined above, and in one particular embodiment is H, and further wherein in this or another preferred embodiment $R_b$ is $CH_3$.

In certain embodiments, the steroid of Formula (I) is selected from the group consisting of:

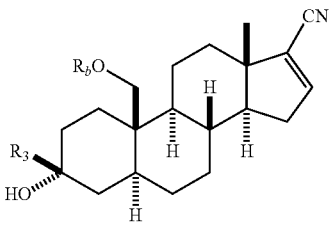

and a pharmaceutically acceptable salt thereof, wherein $R_3$ is as defined above, and in one particular embodiment is H, and further wherein in this or another preferred embodiment $R_b$ is $CH_3$.

In this regard it is to be noted that the structures provided above are of various exemplary embodiments. As such, they should not be viewed in a limiting sense.

2. Prodrug Structure

In another particular embodiment, the present disclosure is in general directed to prodrugs of the various steroids detailed above. Generally speaking, as used herein, a "prodrug" refers to an inactive, or significantly less active, form of the steroids detailed above (and in particular the steroids of Formula (I)), which after administration is metabolized in vivo into one or more active metabolites of the steroid of Formula (I). The prodrug may be formed using means generally known in the art, and therefore may take essentially any form that would be recognized to one of ordinary skill in the art. The prodrugs of the present disclosure may advantageously provide improved absorption, distribution, metabolism and/or excretion optimization, as well as improved oral bioavailability of the steroids detailed above (and in particular the steroids of Formula (I)).

In another particular embodiment of the present disclosure the prodrug of a steroid disclosed herein has a structure of Formula (II):

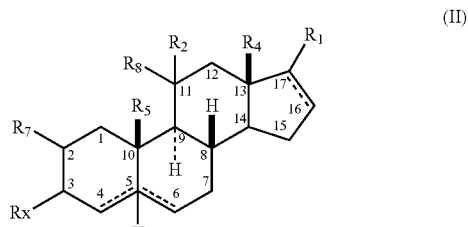

(II)

or a pharmaceutically acceptable salt thereof;
wherein:

$R_1$ is selected from ($C_1$-$C_4$ alkyl)-O (e.g., methoxy, ethoxy, propoxy, butoxy), spirooxirane, cyano, =O, nitro, ($C_1$-$C_4$ alkyl)C(O) (e.g., $CH_3C(O)$, $CH_3CH_2C(O)$, $CH_3CH_2CH_2C(O)$, $CH_3CH_2CH_2CH_2C(O)$), and HO($C_1$-$C_4$ alkyl)C(O) (e.g., $HOCH_2C(O)$, $HOCH_2CH_2C(O)$, $HOCH_2CH_2CH_2C(O)$, $HOCH_2CH_2CH_2CH_2C(O)$), with $R_1$ preferably being in the beta position when other than =O, and/or in one or more preferred embodiments $C_1$-$C_4$ alkyl being methyl, $R_1$ therefore being is selected from methoxy, spirooxirane, cyano, nitro, $CH_3C(O)$— and $OHCH_2C(O)$—;

$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;

$R_x$ is =O or $OR_d$, where $R_d$ is H or $C(O)R_e$, where $R_e$ is optionally substituted $C_1$-$C_{22}$ alkyl or optionally substituted $C_2$-$C_{22}$ alkenyl, with the proviso that when $R_x$ is OH, it is in the beta configuration;

$R_4$ is independently selected from H and unsubstituted $C_1$-$C_4$ alkyl;

$R_5$ is substituted $C_1$-$C_4$ alkyl, optionally substituted $C_2$-$C_4$ alkenyl, or optionally substituted $C_2$-$C_4$ alkynyl (and in particular is alkoxy-substituted methyl, or even more particular is —CH2-ORb, where Rb is $C_1$-$C_4$ alkyl, or even still more particularly is —CH2-OCH3);

$R_6$ is H, optionally substituted $C_1$-$C_4$ alkyl, or optionally substituted $C_1$-$C_4$ alkoxy;

$R_7$ is H, optionally substituted $C_1$-$C_4$ alkoxy, or an optionally substituted morpholinyl ring;

$R_8$, when present, is H or optionally substituted $C_1$-$C_4$ alkyl;

- - - denotes an optional, additional C—C bond, resulting in either a C=C bond between C4-C5 or C5-C6, with the proviso that when present, the C5-H substituent is not present; and,

- - - denotes an optional, additional C—C bond, resulting in a C=C bond between C16-C17, with the proviso that when present, the R1 is not =O, provided that the compound does not have one of the following structures:

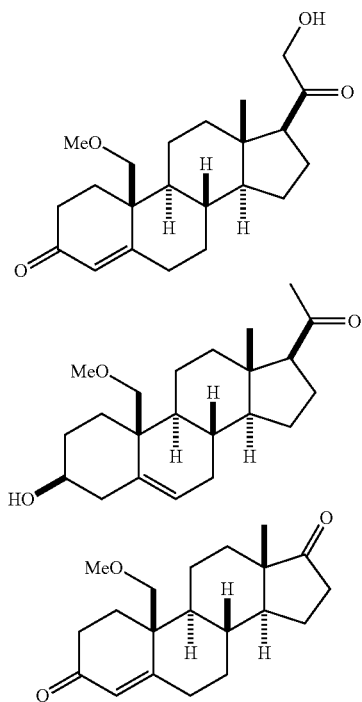

or alternatively provided that: (i) when $R_x$ is =O, a C=C bond is present between $C_4$-$C_5$, and $R_5$ is $CH_2OCH_3$, then $R_1$ is selected from methoxy, spirooxirane, cyano, nitro, and $CH_3C(O)$—; and/or (ii) when $R_x$ is beta-OH, a C=C bond is present between $C_5$-$C_6$, and $R_5$ is $CH_2OCH_3$, then $R_1$ is selected from methoxy, spirooxirane, cyano, nitro, and $HOCH_2C(O)$—.

In this regard, it is to be noted that the present disclosure contemplates and is intended to encompass all of the various combinations and permutations (i.e., combinations of substituent options, locations and stereochemical configurations) possible here.

As generally defined above, R1 is selected from (C1-C4 alkyl)-O, spirooxirane, cyano, =O, nitro, (C1-C4 alkyl)C(O), and HO(C1-C4 alkyl)C(O). In certain embodiments, R1 is preferably in the beta position (when other than =O, or when a C=C is not present between C16-C17). In certain embodiments, $R_1$ is selected from ($C_1$-$C_4$ alkyl)-O (e.g., methoxy, ethoxy, propoxy, butoxy), spirooxirane, cyano, =O, nitro, ($C_1$-$C_4$ alkyl)C(O) (e.g., $CH_3C(O)$, $CH_3CH_2C(O)$, $CH_3CH_2$ $CH_2C(O)$, $CH_3CH_2$ $CH_2$ $CH_2C(O)$), and HO($C_1$-$C_4$ alkyl)C(O) (e.g., $HOCH_2C(O)$, $HOCH_2CH_2C(O)$, $HOCH_2CH_2$ $CH_2C(O)$, $HOCH_2CH_2$ $CH_2$ $CH_2C(O)$). In certain embodiments, $C_1$-$C_4$ alkyl is methyl, $R_1$ therefore being is selected from methoxy, spirooxirane, cyano, =O, nitro, $CH_3C(O)$— and $OHCH_2C(O)$—.

As generally defined above, $R_x$ is =O or $OR_d$, where $R_d$ is H or $C(O)R_e$, where $R_e$ is optionally substituted $C_1$-$C_{22}$ alkyl or optionally substituted $C_2$-$C_{22}$ alkenyl (including for example optionally substituted $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl or $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkenyl), with the proviso that when $R_x$ is OH, it is in the beta (up) configuration. In certain embodiments, $R_x$ is =O. In certain embodiments, $R_x$ is OH in the beta (up) configuration. In certain embodiments, $R_x$ is $OR_d$, $R_d$ is $C(O)R_e$, and $R_e$ is optionally substituted $C_1$-$C_{22}$ alkyl or optionally substituted $C_2$-$C_{22}$ alkenyl, e.g., $C(O)CH_3$, and in such instances, the group Rx is provided in either the alpha or beta configuration (with the beta configuration being preferred). In certain embodiments, wherein $R_x$ is $OR_d$, and $R_d$ is H, then $R_x$ is OH in the beta (up) configuration.

As generally defined above, $R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present. In certain embodiments, $R_2$ is =O and $R_8$ is not present. In certain embodiments, $R_2$ is H. In certain embodiments, $R_2$ is $OR_a$. In certain embodiments, $R_2$ is $OR_a$ and $R_a$ is optionally substituted $C_1$, $C_2$, $C_3$ or $C_4$ alkyl (e.g., methyl, ethyl), optionally substituted benzyl, or $C_1$, $C_2$, $C_3$ or $C_4$ alkyl substituted with O-aryl, such as O-benzyl. In certain embodiments, $R_2$ is $OR_a$ and $R_a$ is optionally substituted aryl. In certain embodiments, $R_2$ is $OR_a$ and $R_a$ is H.

As generally defined above, $R_4$ is H or unsubstituted $C_1$-$C_4$ alkyl. In certain embodiments, $R_4$ is H. In certain embodiments, $R_4$ is unsubstituted $C_1$, $C_2$, $C_3$ or $C_4$ alkyl (e.g., methyl, ethyl, n-propyl, isopropyl, or n-butyl).

As generally defined above, $R_5$ is substituted $C_1$-$C_4$ alkyl, optionally substituted $C_2$-$C_4$ alkenyl, or optionally substituted $C_2$-$C_4$ alkynyl. In certain embodiments, $R_5$ is substituted $C_1$-$C_4$ alkyl, and in particular is alkoxy-substituted $C_1$-$C_4$ alkyl. In other particular embodiments, $R_5$ is substituted methyl, and more particularly is alkoxy-substituted methyl (or even more particularly is —$CH_2$—$OR_b$, where $R_b$ is $C_1$-$C_4$ alkyl, or even still more particularly is —$CH_2$—$OCH_3$). In other embodiments, $R_5$ is optionally substituted $C_2$-$C_4$ alkenyl. In other embodiments, $R_5$ is optionally substituted $C_2$-$C_4$ alkynyl.

As generally defined above, $R_6$ is H, optionally substituted $C_1$-$C_4$ alkyl, or optionally substituted $C_1$-$C_4$ alkoxy. In certain embodiments, $R_6$ is H. In certain embodiments, $R_6$ is optionally substituted $C_1$, $C_2$, $C_3$, or $C_4$ alkyl (e.g., methyl). In certain embodiments, $R_6$ is optionally substituted $C_1$, $C_2$, $C_3$ or $C_4$ alkoxy (e.g., methoxy, ethoxy, n-propyloxy, isopropyloxy, or n-butoxy). In certain embodiments, when $R_6$ is a non-hydrogen group, $R_6$ is in the alpha (down) position. In certain preferred embodiments, however, when $R_6$ is a non-hydrogen group, $R_6$ is in the beta (up) position.

As generally defined above, R7 is H, optionally substituted C1-C4 alkoxy, or an optionally substituted morpholinyl ring. In certain embodiments, R7 is H. In certain embodiments, R7 is optionally substituted C1, C2, C3 or C4 alkoxy (e.g., methoxy, ethoxy, n-propyloxy, isopropyloxy, or n-butoxy). In certain embodiments, R7 is an optionally substituted morpholinyl ring. In certain embodiments, when R7 is a non-hydrogen group, R7 is in the alpha (down) position. In certain preferred embodiments, however, when R7 is a non-hydrogen group, R7 is in the beta (up) position.

As generally defined above, R8, when present, is H or optionally substituted C1-C4 alkyl. In certain embodiments, R8 is H. In certain embodiments, R8 is C1, C2, C3 or C4 optionally substituted alkyl (e.g., methyl). In certain embodiments, when R8 is optionally substituted C1-C4 alkyl, R8 is in the alpha (down) position. In certain embodiments when R8 is optionally substituted C1-C4 alkyl, R8 is in the beta (up) position.

In certain embodiments, R2 and R8 are both H. In certain embodiments, R2 is ORa and R8 is H.

As generally defined above, - - - denotes an optional, additional C—C bond, resulting in either a C═C bond between $C_4$-$C_5$ or $C_5$-$C_6$, with the proviso that when present, the $C_5$—H substituent is not present. In certain embodiments, the additional C—C bond is absent, and the hydrogen at $C_5$ is in the alpha or beta position. In certain embodiments, the additional C—C bond is absent, and the hydrogen at $C_5$ is in the alpha (down) position. In certain embodiments, the additional C—C bond is absent, and the hydrogen at $C_5$ is in the beta (up) position. In certain embodiments, - - - denotes an additional C—C bond, resulting in a C═C bond between $C_4$-$C_5$. In certain embodiments, - - - denotes an additional C—C bond, resulting in a C═C bond between $C_5$-$C_6$.

As generally defined above, - - - denotes an optional, additional C—C bond, resulting in a C═C bond, between C16-C17, with the proviso that when present, the R1 is other than ═O. In certain embodiments, the additional C—C bond is absent (i.e., there is not C═C bond), and therefore R1 may be in the alpha or beta position. In certain embodiments, the additional C—C bond is absent, and the R1 is in the alpha (down) position. In certain embodiments, the additional C—C bond is absent, and the R1 is in the beta (up) position.

In certain embodiments, prodrugs of the present disclosure may be selected from among those encompassed by the structure of Formula (II), wherein R2 is ═O. In certain embodiments, R2 is H and R8 is H, e.g., C11 thus having two hydrogen atoms bound thereto as substituents. In certain embodiments, R2 may be ORa, wherein Ra is methyl, optionally substituted benzyl, or C1-C4 alkyl substituted with O-aryl, such as O-benzyl. In certain embodiments, Rx is ═O. In certain embodiments, Rx is β-hydroxy. In certain embodiments, Rx is ORd, where Rd is H or C(O)Re, where Re is optionally substituted C1-C4 alkyl (e.g., methyl). In certain embodiments, each of R4 and R6 are independently selected from H and methyl. In certain embodiments, R6 is optionally substituted alkyl, e.g., methyl, optionally in the alpha-configuration when the carbon-carbon double bond between C5-C6 is absent. In certain embodiments, R6 is optionally substituted alkyl, e.g., methyl, optionally in the beta-configuration when the carbon-carbon double bond between C5-C6 is absent. In certain embodiments, R7 is selected from H, methoxy, ethoxy, and an optionally substituted morpholinyl ring. In certain embodiments, R7 is a non-hydrogen group, R7 is in the β-position. In certain embodiments, a carbon-carbon double bond (or unsaturated bond) may be present between the C4-C5, or C5-C6, carbon atoms. In certain embodiments, R8, when present, is selected from H or optionally substituted C1-C4 alkyl, preferably methyl and more preferably alpha-methyl.

In certain embodiments, Rx is OH and in the beta position. In certain embodiments, a carbon-carbon double bond is present between the C4-C5 carbon atoms. In certain embodiments, a carbon-carbon double bond is present between the C5-C6 carbon atoms. In certain embodiments, R2 is ═O. In certain embodiments, R2 is methoxy. In certain embodiments, R7 is H. In certain embodiments, R7 is β-methoxy. In certain embodiments, R7 is β-ethoxy.

In certain embodiments, wherein R4 is methyl, R5 is substituted methyl in the beta position, and R6 is H, provided is a compound of Formula (II-a):

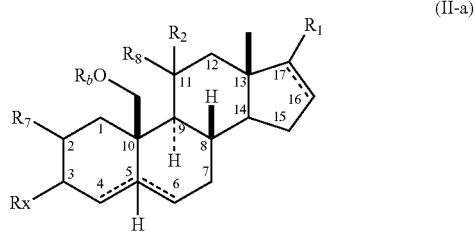

(II-a)

or a pharmaceutically acceptable salt thereof, wherein $R_1$, - - -, $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is ═O. In certain embodiments, $R_x$ is OH in the beta (up) configuration. In certain embodiments, each instance of - - - between $C_5$-$C_6$ and $C_6$-$C_7$ is absent and $C_5$—H is in the alpha position. In certain embodiments, each instance of - - - between $C_5$-$C_6$ and $C_6$-$C_7$ is absent and $C_5$—H is in the beta position. In certain embodiments, - - - represents an additional C—C bond, resulting in either a C═C bond between $C_4$-$C_5$ or $C_5$-$C_6$. In certain embodiments, each instance of - - - between $C_{16}$-$C_{17}$ is absent and $R_1$ is in the beta position. In certain embodiments, - - - represents an additional C—C bond, resulting in a C═C between $C_{16}$-$C_{17}$.

In certain embodiments of Formula (II), wherein $R_2$ is ═O and $R_8$ is absent, provided is a compound of Formula (II-b):

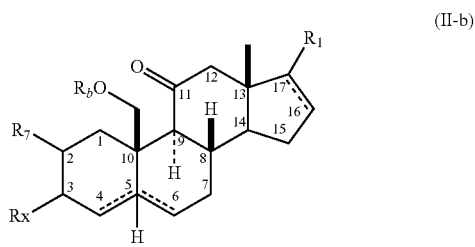

(II-b)

or a pharmaceutically acceptable salt thereof, wherein $R_1$, - - -, $R_x$, and $R_7$ (preferably in the beta configuration) are as defined herein, and further wherein $R_b$ is optionally substituted $C_1$-$C_4$ alkyl. In certain embodiments, $R_x$ is ═O. In certain embodiments, $R_x$ is OH in the beta (up) configuration. In certain embodiments, each instance of - - - between $C_5$-$C_6$ and $C_6$-$C_7$ is absent and $C_5$—H is in the alpha position. In certain embodiments, each instance of - - - between $C_5$-$C_6$ and $C_6$-$C_7$ is absent and $C_5$—H is in the beta position. In certain embodiments, - - - represents an additional C—C bond, resulting in either a C=C bond between $C_4$-$C_5$ or $C_5$-$C_6$. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein $R_2$ is H and $R_8$ is H, provided is a compound of Formula (II-c):

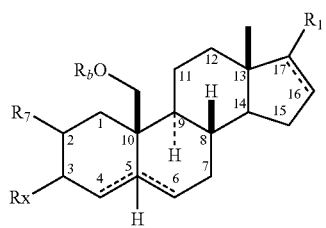

(II-c)

or a pharmaceutically acceptable salt thereof, wherein $R_1$, - - -, $R_x$, and $R_7$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - between $C_5$-$C_6$ and $C_6$-$C_7$ is absent and $C_5$—H is in the alpha position. In certain embodiments, each instance of - - - between $C_5$-$C_6$ and $C_6$-$C_7$ is absent and $C_5$—H is in the beta position. In certain embodiments, - - - represents an additional C—C bond, resulting in either a C=C bond between $C_4$-$C_5$ or $C_5$-$C_6$. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein $R_2$ is $OR_a$ and $R_8$ is H, provided is a compound of Formula (II-d):

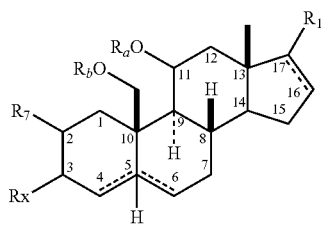

(II-d)

or a pharmaceutically acceptable salt thereof, wherein $R_1$, - - -, $R_3$, $R_7$ (preferably in the beta configuration), and $R_a$ are as defined herein, and further wherein $R_b$ is optionally substituted $C_1$-$C_4$ alkyl. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein $R_7$ is H, provided is a compound of Formula (II-e):

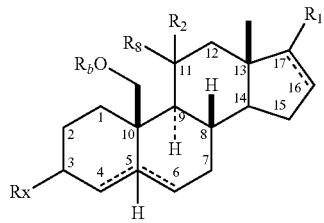

(II-e)

or a pharmaceutically acceptable salt thereof, wherein $R_1$, - - -, $R_x$, $R_2$ and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein each instance of - - - is absent $C_5$—H is in the alpha position, provided is a compound of Formula (II-f):

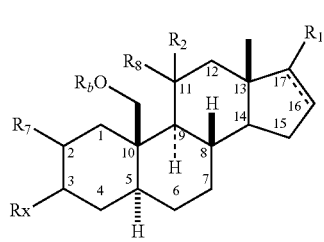

(II-f)

or a pharmaceutically acceptable salt thereof, wherein $R_1$, $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein $R_7$ is H, provided is a compound of Formula (II-g):

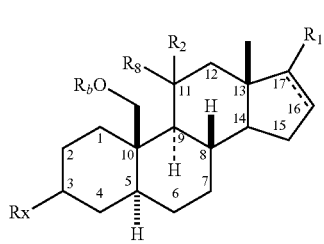

(II-g)

or a pharmaceutically acceptable salt thereof, wherein $R_1$, $R_x$, $R_2$ and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein $R_2$ is =O, provided is a compound of Formula (II-h):

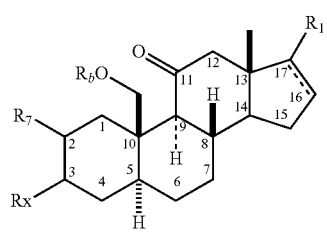

(II-h)

or a pharmaceutically acceptable salt thereof, wherein $R_1$, $R_x$ and $R_7$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein $R_2$ is $OR_a$, provided is a compound of Formula (II-i):

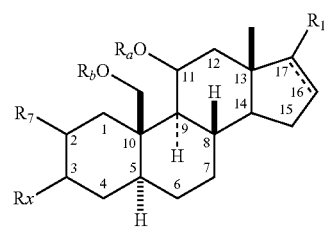

(II-i)

or a pharmaceutically acceptable salt thereof, wherein $R_1$, $R_x$, $R_a$, and $R_7$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein - - - represents an additional C—C bond, resulting in a C=C bond between $C_4$-$C_5$ provided is a compound of Formula (II-j):

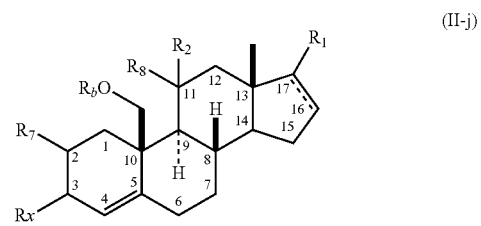

(II-j)

or a pharmaceutically acceptable salt thereof, wherein $R_1$, $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

In certain embodiments of Formula (II), wherein - - - represents an additional C—C bond, resulting in a C=C bond between $C_5$-$C_6$ provided is a compound of Formula (II-k):

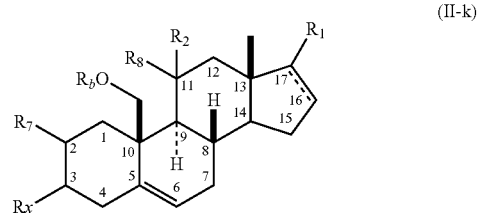

(II-k)

or a pharmaceutically acceptable salt thereof, wherein $R_1$, $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - between $C_{16}$-$C_{17}$ is absent and $R_1$ is in the beta position. In certain embodiments, - - - represents an additional C—C bond, resulting in a C=C between $C_{16}$-$C_{17}$.

It is to be noted that, in one or more of the preferred embodiments detailed above, $R_1$ may, in particular, be selected from methoxy (or more generally lower alkoxy, e.g., —O—($C_1$-$C_4$)), or alternatively selected from $CH_3C$(O)— or $HOCH_2C$(O)— (or more generally substituted or unsubstituted lower alkyl-carbonyl, e.g., ($C_1$-$C_4$)C(O)—, wherein one or more of the carbon atoms is optionally substituted, such as for example by a hydroxyl group). Alternatively, $R_1$ may be selected from nitro or cyano, with an optional C=C being present between $C_{16}$-$C_{17}$. In yet another alternative embodiment, $C_{17}$ may be a carbonyl carbon (i.e., $R_1$ is =O), or it may be part of an oxirane ring fused with the D-ring (i.e., $R_1$ being a spirooxirane substituent, wherein $C_{17}$ is the carbon atom common to both rings).

Exemplary compounds of Formula (II) include, but are not limited to:

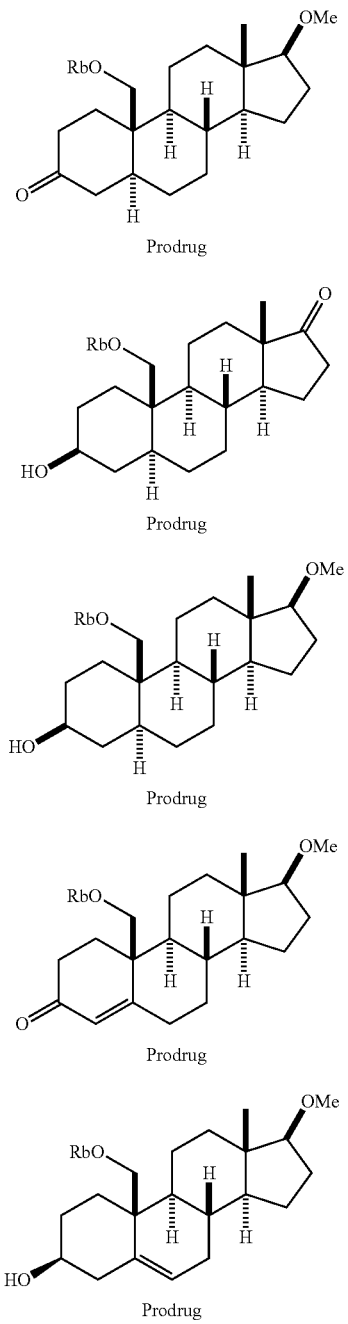

and pharmaceutically acceptable salts thereof, wherein in one preferred embodiment $R_b$ is $CH_3$.

In this regard it is to be noted that the structures provided above are of various exemplary embodiments. As such, they should not be viewed in a limiting sense.

3. Methods of Preparation and Pharmaceutical Compositions

It is to be noted that the compounds or steroids of the present disclosure, or the prodrugs thereof, may in various embodiments be prepared or used in accordance with means generally known in the art. For example, in certain embodiments, the steroids or prodrugs of the present disclosure may be prepared or used in a pharmaceutically acceptable salt form, for example, where $R_7$ is an optionally substituted morpholinyl ring. Suitable salt forms include, for example, citrate or chloride salt forms.

In various embodiments of the present disclosure, a pharmaceutical composition is disclosed that may comprise a steroid, a prodrug, or a combination of two or more thereof in accordance with the formulas of the present disclosure. The compounds or steroids of the present disclosure (or the prodrugs thereof), as well as the various salt forms and other pharmaceutically acceptable forms, e.g., solvates and/or hydrates of compounds described herein, and pharmaceutical compositions containing them, may in general be prepared using methods and techniques known in the art, and/or as described in the Examples provided herein.

Without wishing to be bound by any particular theory, the compounds or steroids of the present disclosure are useful for potentiating GABA at $GABA_A$ receptors thereby inducing anesthesia or treating disorders related to GABA function (e.g., insomnia, mood disorders, convulsive disorders, anxiety disorders, or symptoms of ethanol withdrawal) in a subject, e.g., a human subject, and are preferably administered in the form of a pharmaceutical composition comprising an effective amount of a compound of the instant disclosure and optionally a pharmaceutically or pharmacologically acceptable carrier.

In one aspect, provided is a method of inducing anesthesia in a subject in need thereof, the method comprising administering to the subject a therapeutically effective amount of one or more of the above-noted steroids, or prodrugs, or pharmaceutically acceptable salts thereof, or a pharmaceutical composition thereof.

In another aspect, provided is a method of treating disorders related to GABA function in a subject in need thereof, the method comprising administering to the subject a therapeutically effective amount of one or more of the above-noted steroids, or prodrugs, or pharmaceutically acceptable salts thereof, or a pharmaceutical composition thereof. In certain embodiments, the disorder is selected from the group consisting of insomnia, mood disorders, convulsive disorders, anxiety, or symptoms of ethanol withdrawal.

In one embodiment of the present disclosure, a therapeutically effective amount of compound is from about 5 mg/kg to about 20 mg/kg, about 5 mg/kg to about 18 mg/kg, about 5 mg/kg to about 16 mg/kg, about 5 mg/kg to about 14 mg/kg, about 5 mg/kg to about 12 mg/kg, about 5 mg/kg to about 10 mg/kg, about 6 mg/kg to about 10 mg/kg, about 6 mg/kg to about 9 mg/kg, about 7 mg/kg to about 9 mg/kg, or about 8 mg/kg to about 16 mg/kg. In certain embodiments, a therapeutically effective amount of the compound is about 8 mg/kg. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The exact amount of a compound required to achieve an effective amount will vary from subject to subject, depending, for example, on species, age, and general condition of a subject, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body.

The compound or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Exemplary therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

The pharmaceutical composition may also be in combination with at least one pharmacologically acceptable carrier. The carrier, also known in the art as an excipient, vehicle, auxiliary, adjuvant, or diluent, is any substance that is pharmaceutically inert, confers a suitable consistency or form to the composition, and does not diminish the therapeutic efficacy of the compounds. The carrier is "pharmaceutically or pharmacologically acceptable" if it does not produce an adverse, allergic, or other untoward reaction when administered to a mammal or human, as appropriate.

The pharmaceutical compositions containing the compounds or steroids of the present disclosure may be formulated in any conventional manner. Proper formulation is dependent upon the route of administration chosen. The compositions of the disclosure can be formulated for any route of administration, so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration. In certain embodiments, the route of administration is oral. In certain embodiments, the route of administration is parenteral. In certain embodiments, the route of administration is intravenous.

Pharmaceutically acceptable carriers for use in the compositions of the present disclosure are well known to those of ordinary skill in the art and are selected based upon a number of factors, including for example: the particular compound used, and its concentration, stability and intended bioavailability; the disease, disorder or condition being treated with the composition; the subject, its age, size and general condition; and/or the route of administration. Suitable carriers may be readily determined by one of ordinary skill in the art. (See, for example, J. G. Nairn, in: Remington's Pharmaceutical Science (A. Gennaro, ed.), Mack Publishing Co., Easton, Pa., (1985), pp. 1492-1517.)

The compositions may be formulated as tablets, dispersible powders, pills, capsules, gelcaps, caplets, gels, liposomes, granules, solutions, suspensions, emulsions, syrups, elixirs, troches, dragees, lozenges, or any other dosage form that can be administered orally. Techniques and compositions for making oral dosage forms useful in the present disclosure are described in the following exemplary references: 7 Modern Pharmaceutics, Chapters 9 and 10 (Banker & Rhodes, Editors, 1979); Lieberman et al., Pharmaceutical Dosage Forms: Tablets (1981); and, Ansel, Introduction to Pharmaceutical Dosage Forms 2nd Edition (1976).

The compositions of the present disclosure designed for oral administration comprise an effective amount of a compound of the disclosure in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques (e.g., to delay disintegration and absorption).

The compounds, steroids, and prodrugs of the present disclosure may also be formulated for parenteral administration (e.g., formulated for injection via intravenous, intraarterial, subcutaneous, rectal, subcutaneous, intramuscular, intraorbital, intracapsular, intraspinal, intraperitoneal, or intrasternal routes). The compositions of the present disclosure for parenteral administration comprise an effective amount of the compound in a pharmaceutically acceptable carrier. Dosage forms suitable for parenteral administration include solutions, suspensions, dispersions, emulsions or any other dosage form that can be administered parenterally. Techniques and compositions for making parenteral dosage forms are known in the art. Typically formulations for parenteral administration are sterile or are sterilized before administration.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)30-60 sorbitol poly(oleate)2-4, poly(oxyethylene)15-20 monooleate, poly(oxyethylene)15-20 mono 12-hydroxystearate, and poly(oxyethylene)15-20 mono-ricinoleate, polyoxyethylene sorbitan esters (such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del.), polyvinylpyrrolidone, alkyleneoxy modified fatty acid esters (such as polyoxyl 40 hydrogenated castor oil, cyclodextrins or modified cyclodextrins (e.g., beta-hydroxypropyl-cyclodextrin)), saccharide fatty acid esters (i.e., the condensation product of a monosaccharide (e.g., pentoses, such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a C4-C22 fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the disclosure are well known to those of ordinary skill in the art, and are identified in The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.)(Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.,) (Marcel Dekker, Inc., New York, N.Y., 1980), Remington's Pharmaceutical Sciences (A. Gennaro, ed., 19th ed.)(Mack Publishing, Easton, Pa., 1995), The United States Pharmacopeia 24, The National Formulary 19, (National Publishing, Philadelphia, Pa., 2000), A. J. Spiegel et al., and Use of Nonaqueous Solvents in Parenteral Products, J. of Pharm. Sciences, Vol. 52, No. 10, pp. 917-927 (1963).

Preferred solvents include cyclodextrins or modified cyclodextrins (e.g., beta-hydroxypropyl-cyclodextrin) as well as oils rich in triglycerides, for example, safflower oil, soybean oil or mixtures thereof, and alkyleneoxy modified fatty acid esters such as polyoxyl 40 hydrogenated castor oil. Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®.

Additional minor components can be included in the compositions of the disclosure for a variety of purposes well known in the pharmaceutical industry. These components will for the most part impart properties which enhance retention of the compound at the site of administration, protect the stability of the composition, control the pH, facilitate processing of the compound into pharmaceutical formulations, and the like. Preferably, each of these components is individually present in less than about 15 wt % of the total composition, more preferably less than about 5 wt %, and most preferably less than about 0.5 wt % of the total composition. Some components, such as fillers or diluents, can constitute up to 90 wt % of the total composition, as is well known in the formulation art. Such additives include cryoprotective agents for preventing reprecipitation, surface active, wetting or emulsifying agents (e.g., lecithin, polysorbate-80, Tween® 80, Pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfate, sodium sulfite, dextrose, phenols, and thiophenols).

Dosage from administration by these routes may be continuous or intermittent, depending, for example, upon the patient's physiological condition, whether the purpose of the administration is therapeutic or prophylactic, and other factors known to and assessable by a skilled practitioner.

Those with ordinary skill in administering anesthetics can readily determine dosage and regimens for the administration of the pharmaceutical compositions of the disclosure or titrating to an effective dosage for use in treating insomnia, mood disorders, convulsive disorders, anxiety or symptoms of ethanol withdrawal. It is understood that the dosage of the compounds will be dependent upon the age, sex, health, and weight of the recipient, kind of concurrent treatment, if any, frequency of treatment, and the nature of the effect desired. For any mode of administration, the actual amount of compound delivered, as well as the dosing schedule necessary to achieve the advantageous effects described herein, will also depend, in part, on such factors as the bioavailability of the compound, the disorder being treated, the desired therapeutic dose, and other factors that will be apparent to those of skill in the art. The dose administered to an animal, particularly a human, in the context of the present disclosure should be sufficient to affect the desired therapeutic response in the animal over a reasonable period of time. Preferably, an effective amount of the compound, whether administered orally or by another route, is any amount that would result in a desired therapeutic response when administered by that route. The dosage may vary depending on the dosing schedule, which can be adjusted as necessary to achieve the desired therapeutic effect. The most preferred dosage will be tailored to the individual subject, as is understood and determinable by one of ordinary skill in the art without undue experimentation.

In one embodiment, solutions for oral administration are prepared by dissolving the compound in any pharmaceutically acceptable solvent capable of dissolving a compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as beta-hydroxypropyl-cyclodextrin. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsions, is added to the solution while stirring to form a pharmaceutically acceptable emulsion for parenteral administration to a patient.

Solutions for parenteral administration can be prepared by dissolving a compound in any pharmaceutically acceptable solvent capable of dissolving the compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for parenteral administration to a patient.

If desired, the emulsions or solutions described above for oral or parenteral administration can be packaged in IV bags, vials or other conventional containers in concentrated form and diluted with any pharmaceutically acceptable liquid, such as saline, to form an acceptable concentration prior to use as is known in the art.

Still further encompassed by the invention are kits (e.g., pharmaceutical packs). The kits provided may comprise a compound as described herein and a container (e.g., a vial, ampule, bottle, syringe, and/or dispenser package, or other suitable container). In some embodiments, provided kits may optionally further include a second container comprising a pharmaceutical carrier for dilution or suspension of the pharmaceutical composition or compound. In some embodiments, the pharmaceutical composition or compound provided in the container and the second container are combined to form one unit dosage form.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

4. Definitions

The term "steroid" as used herein describes an organic compound containing in its chemical nucleus the cyclopenta[α]phenanthrene ring system.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "prodrug" as used herein describes a pharmacological substance that is administered in a less active or inactive form. After administration, a prodrug is metabolized in vivo e.g., via hydrolysis, oxidation, or reaction under biological conditions (in vitro or in vivo), to provide an active metabolite. See, e.g., Wu, Pharmaceuticals (2009) 2:77-81. In certain embodiments, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract or the skin, or it may enhance drug stability for long-term storage.

As used herein, a "subject" to which administration is contemplated includes, but is not limited to, mammals, e.g., humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the invention, the subject is a human.

As used herein, a "therapeutically effective amount", "an amount sufficient" or "sufficient amount" of a compound means the level, amount or concentration of the compound required for a desired biological response, e.g., analgesia.

The term "saturated" as used herein describes the state in which all available valence bonds of an atom (especially carbon) are attached to other atoms.

The term "unsaturated" as used herein describes the state in which not all available valence bonds along the alkyl chain are satisfied; in such compounds the extra bonds usually form double or triple bonds (chiefly with carbon).

When a range of values is listed, it is intended to encompass each value and sub-range within the range. For example "C1-4 alkyl" is intended to encompass, C1, C2, C3, C4, C1-3, C1-2, C2-4, C2-3 and C3-4 alkyl, while "C1-22 alkyl" is intended to encompass, for example, C1, C2, C3, C4, etc., as well as C1-21, C1-20, C1-15, C1-10, C2-20, C2-15, C2-10, C3-15, C3-10, etc. alkyl.

As used herein, "alkyl" refers to a radical of a straight-chain or branched saturated hydrocarbon group having from, in some embodiments, 1 to 4 carbon atoms ("C1-4 alkyl"), and in other embodiments 1 to 22 carbon atoms ("C1-22 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 4 carbon atom ("C2-4 alkyl"). In yet other embodiments, an alkyl group has 1 to 21 carbon atoms ("C1-21 alkyl"), 1 to 20 carbon atoms ("C1-20 alkyl"), 1 to 15 carbon atoms ("C1-15 alkyl"), 1 to 10 carbon atoms ("C1-10 alkyl"), etc. Examples of such alkyl groups include methyl (C1), ethyl (C2), n-propyl (C3), isopropyl (C3), n-butyl (C4), tert-butyl (C4), sec-butyl (C4), iso-butyl (C4), pentyl (C5), and the like.

As used herein, "alkenyl" or "alkene" refers to a radical of a straight-chain or branched hydrocarbon group having from, in some embodiments, 2 to 4 carbon atoms ("C2-4 alkenyl"), and in other embodiments 2 to 22 carbon atoms ("C2-22 alkenyl"), and one or more carbon-carbon double bonds. In some embodiments, an alkenyl group has 2 to 3 carbon atoms ("C2-3 alkenyl"). In some embodiments, an alkenyl group has 2 carbon atoms ("C2 alkenyl"). In yet other embodiments, an alkenyl group has 2 to 21 carbon atoms ("C2-21 alkenyl"), 2 to 20 carbon atoms ("C2-20 alkenyl"), 2 to 15 carbon atoms ("C2-15 alkenyl"), 2 to 10 carbon atoms ("C2-10 alkyl"), etc. The one or more carbon-carbon double bonds can be internal (such as in 2-butenyl) or terminal (such as in 1-butenyl). Examples of such alkenyl groups include ethenyl (C2), 1-propenyl (C3), 2-propenyl (C3), 1-butenyl (C4), 2-butenyl (C4), butadienyl (C4), 1-pentenyl (C5), 2-pentenyl (C5), and the like.

As used herein, "alkynyl" or "alkyne" refers to a radical of a straight-chain or branched hydrocarbon group having from 2 to 4 carbon atoms and one or more carbon-carbon triple bonds ("C2-10 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl (C3), 2-propynyl (C3), 1-butynyl (C4), 2-butynyl (C4), and the like.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("C6-14 aryl"). In some embodiments, an aryl group has 6 ring carbon atoms ("C6 aryl"; e.g., phenyl). In some embodiments, an aryl group has 10 ring carbon atoms ("C10 aryl"; e.g., naphthyl such as 1-naphthyl and 2-naphthyl). In some embodiments, an aryl group has 14 ring carbon atoms ("C14 aryl"; e.g., anthracyl).

As used herein, "alkoxy" refers to an alkyl, alkenyl, or alkynyl group, as defined herein, attached to an oxygen radical.

Alkyl, alkenyl, alkynyl, and aryl groups, as defined herein, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents include groups that contain a heteroatom (such as nitrogen, oxygen, silicon, phosphorous, boron, sulfur, or a halogen atom), halogen (e.g., chlorine, bromine, fluorine, or iodine), a heterocycle, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

Methods of Treatment

Earlier studies (see, e.g., Gee et al., European Journal of Pharmacology, 136:419-423 (1987)) demonstrated that certain 3α-hydroxylated steroids are orders of magnitude more potent as modulators of the GABA receptor complex (GRC) than others had reported (see, e.g., Majewska et al., Science 232:1004-1007 (1986); Harrison et al., J Pharmacol. Exp. Ther. 241:346-353 (1987)). Majewska et al. and Harrison et al. taught that 3β-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., European Journal of Pharmacology, 136:419-423 (1987); Wieland et al., Psychopharmacology 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in Central Nervous System Disorders, Horvell, ed., Marcel-Dekker, New York (1985), pp. 123-147; Lloyd, K. G. and Morselli, P. L., "Psychopharmacology of GABAergic Drugs," in Psychopharmacology: The Third Generation of Progress, H. Y. Meltzer, ed., Raven Press, N.Y. (1987), pp. 183-195; and Gee et al., European Journal of Pharmacology, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In an embodiment, disclosed herein are methods of treating a condition related to GABAA receptor modulation by administering to a subject an effective amount of a compound described herein. Exemplary conditions related to GABAA receptor modulation include, but are not limited to: (a) Neurological disorders including sleep disorders [e.g., insomnia and REM sleep behaviour disorder], epilepsy [e.g., status epilepticus, monogenic forms of epilepsy (e.g., Dravet syndrome), Lennox-Gastaut syndrome, infantile spasms, juvenile myoclonic epilepsy, acute repetitive seizures, febrile seizure], movement disorders [e.g., Huntington's disease, Parkinson's disease, cerebellar ataxia, Friedrich's ataxia, Stiff-Person syndrome, dystonia, Tourette Syndrome, essential tremor], traumatic brain injury, pain disorders [e.g., neuropathic pain, injury related chronic pain, acute pain, migraine headache, status migrainosus], vascular disorders [e.g., stroke, ischemia, sequelae of vascular malformations], neurodegenerative disorders [e.g., Alzheimer's disease, Lewy body dementia, frontotemporal dementia, multiple-system atrophy, multi-infarct dementia] and tinnitus; (b) Psychiatric disorders including schizophrenia and schizoaffective disorder, mood disorders [e.g., depression, dysthymic disorder, bipolar disorder, anxiety disorders (e.g., generalized anxiety disorder, social anxiety disorder, phobia, obsessive compulsive disorder, panic disorder, post-traumatic stress disorder), stress], cognitive disorders [e.g., attention deficit hyperactivity disorder], personality disorders [e.g., antisocial personality disorder, obsessive compulsive personality disorder], autism spectrum disorders [e.g., idiopathic autism, monogenic causes of autism (e.g., Rett syndrome, tuberous sclerosis complex, fragile X syndrome, Angleman's syndrome)] and substance abuse disorders [e.g., opiate addiction, stimulant addiction (e.g., cocaine addiction), alcohol addiction]; (c) Women's health disorders including postpartum depression, postpartum dysphoric disorder, polycystic ovarian syndrome, catamenial epilepsy, preterm labor, preeclampsia, eclampsia, premenstrual and menstrual migraine; (d) Inflammatory disorders including multiple sclerosis, asthma and rheumatoid arthritis; (e) Anesthesiology indications comprising the full spectrum of sedation including mild sedation/anxiolysis, moderate/procedural sedation, monitored anesthesia care, deep sedation, general anesthesia.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In certain embodiments, the compound is administered to the subject chronically. In certain embodiments, the compound is administered to the subject orally, subcutaneously, intramuscularly, or intravenously.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are unaffected.

Moderate sedation/analgesia (conscious sedation) is a drug-induced depression of consciousness during which the patient responds purposefully to verbal command, either alone or accompanied by light tactile stimulation. No interventions are necessary to maintain a patent airway. Spontaneous ventilation is adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired. The patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired. Assistance is often required in maintaining a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It plays a pivotal role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Anxiety Disorders

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxymal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

Epilepsy is a brain disorder characterized by repeated seizures overtime. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, and super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles. Atonic seizures consist of a sudden and general loss of muscle tone, particularly in the arms and legs, which often results in a fall.

Autism

Autism is a neurobehavioral developmental syndrome that arises in early childhood and is comprised of a combination of social deficits, limited verbal and/or non-verbal communication, and restricted, repetitive, and stereotyped patterns of behavior, interests or activities. Autism spectrum disorder as defined by the American Psychiatric Association diagnostic and statistical manual of mental disorders (DSMV) incorporates autism, Asperger syndrome, childhood disintegrative disorder, and pervasive developmental disorder not otherwise specified (PDD-NOS).

Autism has an onset before the age of three. This implies that there is a period of normal development after which there is a period of regression.

Asperger syndrome is comprised by social deficits and restricted, repetitive and stereotyped interests without a delay in language development or cognitive delay.

Childhood disintegrative disorder is a milder form of autistic regression with an onset after 3 years of age.

PDD-NOS is characterized by milder symptoms than autism in only one domain (e.g., social deficits).

Autism spectrum disorder can be idiopathic. However, there are many genetic causes of autism including single gene mutations with a high degree of penetrance [e.g., Rett syndrome, tuberous sclerosis complex, fragile X syndrome, Angleman's syndrome]. In some cases, the genetic mutation alone is used to refer to the disease [e.g., 22q13.3 deletion syndrome].

EXAMPLES

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Example.

A. Compound Chemistry

In accordance with the following methods and Examples, the following compounds were prepared for purposes of illustration:

Scheme 1

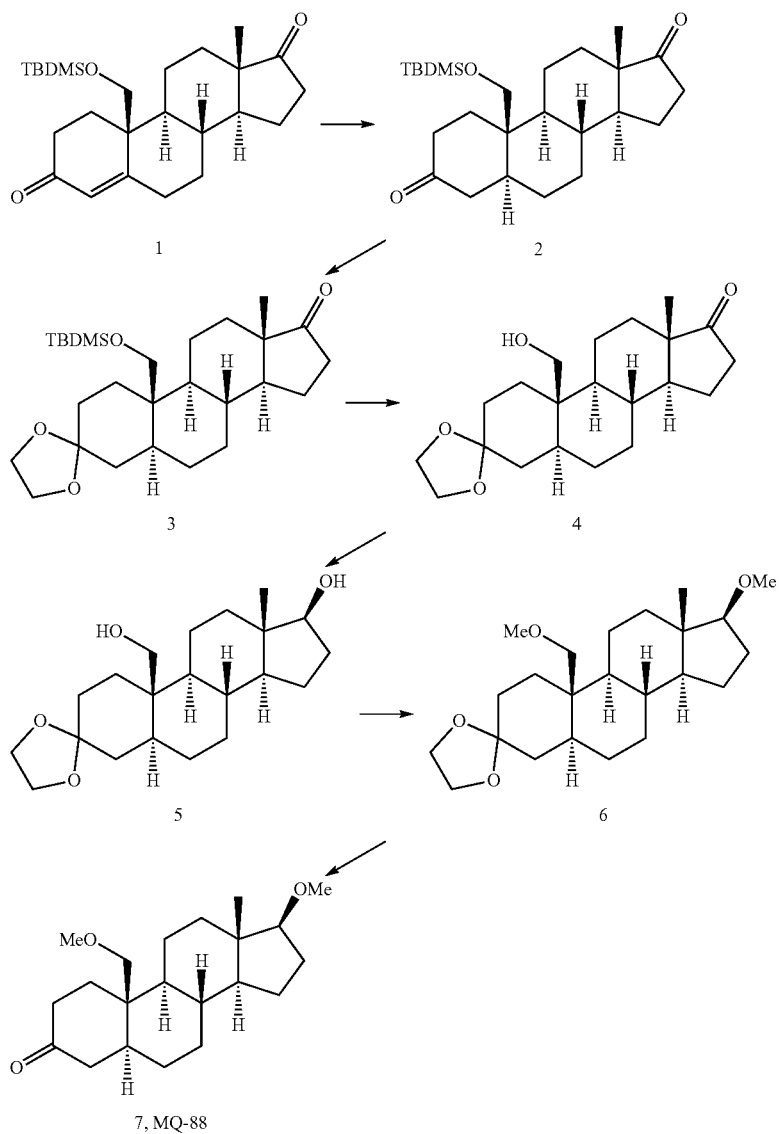

In accordance with Scheme 1, the following compounds were prepared, using methods generally known in the art and as outlined below.

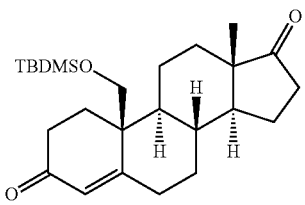

19-[[(1,1-Dimethyl)dimethylsilyl]oxy]-androst-4-ene-3,17-dione (1)

A mixture of the known 19-hydroxyandrostenedione (1 g, 3.31 mmol), tert-butyldimethylsilyl chloride (602 mg, 4 mmol), imidazole (315 mg, 4.63 mmol), DMF (5 mL) and methylene chloride (5 mL) was stirred at room temperature for 15 h. Water (100 mL) was added to the reaction mixture and extracted with methylene chloride (50 mL×3). The combined organic extracts were washed with brine, dried and concentrated to give a white solid. The solid was purified by flash column chromatography (silica gel eluted with 10-20% EtOAc in hexanes) to give a white solid (1.3 g, 94%): mp 154-156° C.; IR 2856, 2930, 1739, 1670, 1472, 1359, 1255, 1228 cm$^{-1}$; $^1$H NMR (CDCl$_3$) δ 5.85 (s, 1H), 3.87 (dd, J=12.9, 10.0 Hz, 2H), 2.65-0.95 (m), 0.89 (s, 3H), 0.83 (s, 9H), 0.03 (s, 3H), 0.02 (s, 3H); $^{13}$C NMR (CDCl$_3$) δ 220.0, 199.6, 167.2, 126.0, 65.8, 54.0, 51.3, 47.5, 43.5, 35.9, 35.6, 34.6, 33.5, 33.2, 31.7, 30.7, 25.7 (3×C), 21.6, 20.9, 18.0, 13.8, −5.76, −5.83.

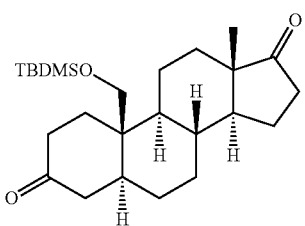

(5α)-19-[[(Dimethylethyl)dimethylsilyl]oxy]-androstane-3,17-dione (2)

Lithium wire in small pieces (140 mg, 20 mmol) was added to a stirred cold solution (−78° C.) of freshly condensed liquid ammonia (250 mL) and the mixture was stirred for 15 min. Steroid 1 (1.25 g, 3 mmol) in THF (75 mL) was added to the resulting deep blue solution and stirring was continued at −78° C. for 2 h. Solid ammonium chloride (5 g) was added and the ammonia was allowed to evaporate. Water (200 mL) was added and the reaction mixture was extracted with EtOAc (100 mL×3). The combined EtOAc extracts were washed with brine, dried and concentrated to give an oil. The oil was dissolved in stirred acetone (50 mL) and cooled in an ice bath. Jones reagent was added to the stirred cold solution until an orange color persisted for 1 h. The excess Jones reagent was reduced by adding few drops of isopropyl alcohol. The acetone was removed under reduced pressure and the resulting solution was diluted with water (200 mL) and extracted with EtOAc (80 mL×3). The combined EtOAc extracts were dried and removed to give a white solid which was purified by chromatography (silica gel) to yield steroid 2 (830 mg, 63%): mp 130-132° C.; IR 3339, 2922, 2857, 1445, 1360 cm$^{-1}$; $^1$H NMR (CDCl$_3$) δ 3.87 (dd, J=21.2, 10.0 Hz, 2H), 2.60-0.70 (m), 0.87 (s, 9H), 0.07 (s, 3H), 0.06 (s, 3H); $^{13}$C NMR (CDCl$_3$) δ 220.6, 211.8, 60.9, 54.3, 51.6, 47.7, 46.1, 44.8, 39.4, 38.5, 35.7, 35.4, 33.9, 31.9, 30.5, 28.3, 25.7 (3×C), 21.7, 18.0, 13.8, −5.7, −5.9.

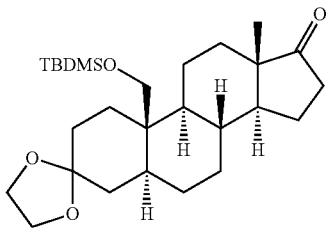

(5α)-19-[[(Dimethylethyl)dimethylsilyl]oxy]-androstane-3,17-dione, 3-cyclic 1,2-ethandiyl acetal (3)

A solution of steroid 2 (4.6 g, 11.0 mmol) in benzene (~100 mL) containing ethylene glycol (5 mL) and PPTS (500 mg) was heated under reflux with Dean-Stark apparatus for 4 h. The solvent was removed under reduced pressure and the residue was purified by column chromatography (silica gel eluted with 20% EtOAc in hexanes) to give the 3,17-bisketal (3.5 g) and steroid 3 as a solidified foam (1.25 g): $^1$H NMR (CDCl$_3$) δ 3.85-3.90 (m, 4H), 3.81 (d, J=10.6 Hz, 1H), 3.65 (d, J=10.6 Hz, 1H), 2.36-0.76 (m), 0.83 (s, 9H), 0.10 (d, J=3.9 Hz, 6H); $^{13}$C NMR (CDCl$_3$) δ 221.2, 109.1, 64.1, 60.3, 59.9, 54.5, 51.8, 47.8, 43.6, 39.2, 38.3, 35.7, 35.4, 32.0, 31.3, 30.7, 30.6, 27.8, 25.7, 21.7, 20.9, 17.0, 14.1, −5.7, −5.9; Anal. Calcd for C$_{27}$H$_{46}$O$_4$Si: C, 70.08; H, 10.02. Found: C, 69.89; H, 10.0.

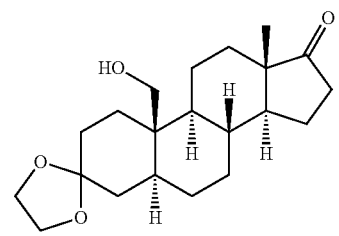

(5α)-19-Hydroxyandrostane-3,17-dione, 3-cyclic 1,2-ethandiyl acetal (4)

To a solution of steroid 3 (1.0 g, 2.4 mmol) in THF (10 mL) was added TBAF (6.0 mmol, 1.0 M in THF, 6.0 mL) at room temperature. The reaction mixture was refluxed for 16 h and the solvent was removed under reduced pressure and the residue was purified by column chromatography (silica gel eluted with 30% EtOAc in hexanes) to give steroid 4 as an oil (638 mg, 84%): IR $v_{max}$ 3487, 1738 cm$^{-1}$; $^1$H NMR (CDCl$_3$) δ 3.90-3.85 (m, 4H), 3.86 (d, J=11.4 Hz, 1H), 3.78 (d, J=11.4 Hz, 1H), 2.42-0.76 (m), 0.86 (s, 3H); $^{13}$C NMR (CDCl$_3$) δ 221.4, 108.9, 64.1, 64.0, 60.0, 54.4, 51.6, 47.8, 43.7, 39.2, 38.2, 35.7, 35.4, 31.9, 31.4, 30.6, 30.1, 27.7, 21.9, 21.7, 13.9.

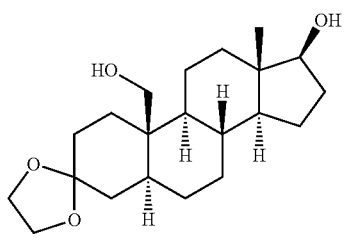

(5α,17β)-17,17-Dihydroxyandrostan-3-one, cyclic 1,2-ethandiyl acetal (5)

To a solution of steroid 4 (635 mg, 1.8 mmol) in ethanol (40 mL) was added sodium borohydride (152 mg, 4 mmol) at room temperature. After 3 h, the mixture was quenched by aqueous NH$_4$Cl. The mixture was extracted with EtOAc (50 mL×3), the organic layers were combined and dried over MgSO$_4$, filtered, and concentrated. The residue was purified by column chromatography (silica gel eluted with 35% EtOAc in hexanes) to give steroid 5 as an oil (638 mg, 100%): $^1$H NMR (CDCl$_3$) δ 3.92-3.90 (m, 5H), 3.90 (d, J=12.4 Hz, 1H), 3.61 (t, J=8.6 Hz, 1H), 2.22-0.73 (m), 0.76 (s, 3H); $^{13}$C NMR (CDCl$_3$) δ 109.1, 81.8, 64.2, 64.1, 60.2, 54.4, 51.3, 43.8, 43.1, 39.3, 38.3, 37.2, 36.0, 31.6, 31.3, 30.4, 30.1, 27.9, 23.4, 22.5, 11.4.

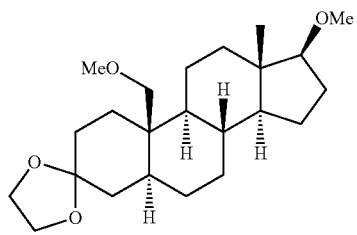

(5α,17β)-17,19-Dimethoxyandrostan-3-one, cyclic 1,2-ethandiyl acetal (6)

To a solution of steroid 5 (635 mg, 1.8 mmol) in THF (30 mL) was added sodium hydride (400 mg, 60% in mineral oil, 6.0 mmol). After addition, the mixture was refluxed for 1 h, iodomethane was added and refluxed for an additional 3 h. After cooling down to room temperature, the mixture was quenched by water and extracted with EtOAc (100 mL×3). The organic extracts were combined and dried over with MgSO$_4$, filtered, and concentrated. The residue was purified by column chromatography (silica gel eluted with 20% EtOAc in hexanes) to give steroid 6 (623 mg, 92%): mp 102-104° C.; IR ν$_{max}$ 2922, 1448 cm$^{-1}$; $^1$H NMR (CDCl$_3$) δ 3.84 (m, 4H), 3.43 (d, J=9.4 Hz, 1H), 3.36 (d, J=9.4 Hz, 1H), 3.24 (s, 3H), 3.21 (s, 3H), 3.12 (t, J=7.8 Hz, 1H), 2.10-0.63 (m), 0.68 (3H); $^{13}$C NMR (CDCl$_3$) δ 109.1, 90.6, 70.9, 64.0 (2×C), 58.9, 57.6, 54.2, 51.3, 43.7, 42.9, 38.8, 38.3, 38.2, 35.6, 31.4, 31.3, 30.9, 28.0, 27.5, 23.2, 21.9, 11.5.

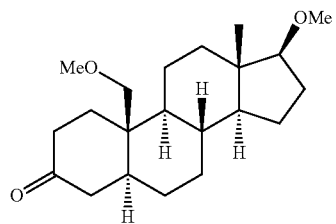

(5α,17β)-17,19-Dimethoxyandrostan-3-one (7, MQ-88)

The mixture of steroid 6 (625 mg, 1.65 mmol), PTSA (100 mg), acetone (30 ml) and water (3 mL) was stirred at room temperature for 16 h. Solvents were removed by reduced pressure, aqueous NaHCO$_3$ was added and the product extracted into EtOAc (100 mL×3). The organic layers were combined, dried over with MgSO$_4$, filtered, and concentrated. The residue was purified by column chromatography (silica gel eluted with 20% EtOAc in hexanes) to give steroid 7 (408 mg, 74%): mp 91-93° C.; [α]$_D^{20}$=18.4 (c=0.37, CHCl$_3$); ν$_{max}$ 2922, 1714 cm$^{-1}$; $^1$H NMR (CDCl$_3$) δ 3.60 (d, J=10.2 Hz, 1H), 3.55 (d, J=9.7 Hz, 1H), 3.24 (s, 6H), 3.12 (t, J=8.2 Hz, 1H), 2.45-0.64 (m), 0.70 (s, 3H); $^{13}$C NMR (CDCl$_3$) δ 212.1, 90.4, 71.8, 59.0, 57.6, 54.0, 51.2, 46.3, 44.8, 42.8, 38.8, 38.7, 38.0, 35.5, 34.3, 31.0, 28.3, 27.5, 23.1, 21.8, 11.5. Anal. Calcd for C$_{21}$H$_{34}$O$_3$: C, 75.41; H, 10.25. Found: C, 75.37; H, 10.13.

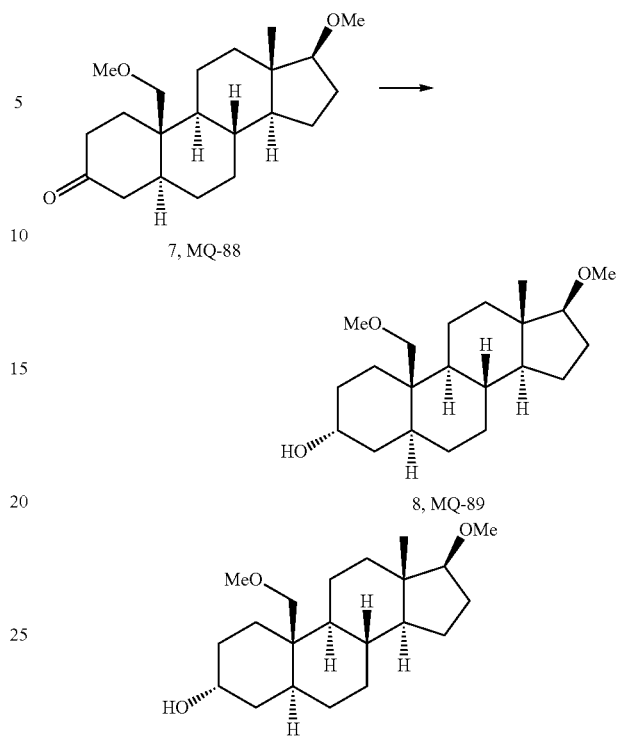

(5α,17β)-17,19-Dimethoxyandrostan-3-ol (8, MQ-89)

To a solution of steroid 7 (200 mg, 0.60 mmol) in THF (10 mL) was added K-selectride® (1.0 mmol, 1.0 M in THF, 1.0 mL) at −78° C. After 2 h, 3 N NaOH (10 mL) and H$_2$O$_2$ (5 mL) were added at −78° C. and the reaction was allowed to warm up to room temperature for 1 h. The product was extracted into EtOAc (100 mL×2) and washed with brine. The organic layers were combined and dried over MgSO$_4$, filtered, and concentrated. The residue was purified by column chromatography (silica gel eluted with 20% EtOAc in hexanes) to give steroid 8 (172 mg, 86%): mp 62-64° C.; [α]$_D^{20}$=1.1 (c=0.26, CHCl$_3$); ν$_{max}$ 3382, 1447 cm$^{-1}$; $^1$H NMR (CDCl$_3$) δ 4.10-4.05 (m, 1H), 3.50 (d, J=10.2 Hz, 1H), 3.42 (d, J=9.8 Hz, 1H), 3.33 (s, 3H), 3.29 (s, 3H), 3.23 (t, J=8.2 Hz, 1H), 2.01-0.80 (m), 0.76 (s, 3H); $^{13}$C NMR (CDCl$_3$) δ 90.9, 71.1, 66.4, 59.1, 57.8, 54.7, 51.6, 43.0, 39.6, 39.3, 38.5, 36.2, 35.8, 31.5, 29.5, 28.1, 27.7, 27.0, 23.3, 21.7, 11.7. Anal. Calcd for C$_{21}$H$_{36}$O$_3$: C, 74.95; H, 10.78. Found: C, 75.19; H, 10.79.

Scheme 3

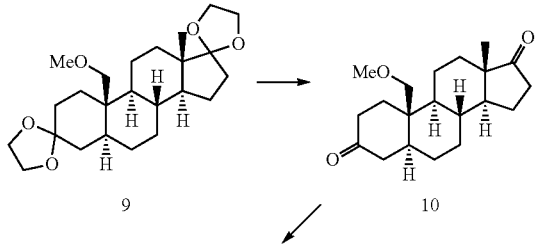

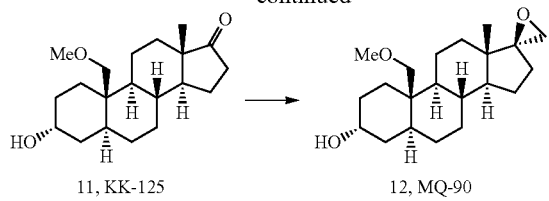

11, KK-125   12, MQ-90

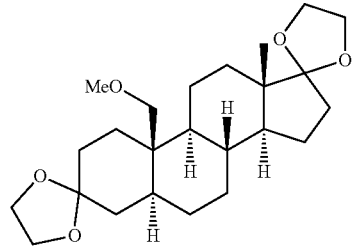

(5α)-19-Methoxyandrostane-3,17-dione, cyclic bis-(1,2-ethanediyl) acetal (9)

A mixture of the known (5α)-19-hydroxyandrostane-3,17-dione, cyclic bis-(1,2-ethanediyl) acetal (430 mg, 1.1 mmol), NaH (200 mg, 5 mmol) and THF (10 mL) was heated at reflux for 2 h under $N_2$. The reaction mixture was cooled to room temperature, and methyl iodide (2 mL, 32 mmol) was added and the mixture was stirred at room temperature for 13 h. The reaction mixture was cooled to 0° C. and excess NaH was carefully quenched by adding MeOH (2 mL). Water (100 mL) was added and the product was extracted into EtOAc (80 mL×3). The combined organic extracts were washed with brine, dried and concentrated to give a colorless liquid. The crude product was purified by flash column chromatography (silica gel eluted with 15-20% EtOAc in hexanes) to give the product as a colorless liquid (440 mg, 99%): IR $v_{max}$ 2923, 1457, 1378, 1306, 1210 cm$^{-1}$; $^1$H NMR δ 3.89 (s, 4H), 3.87-3.82 (m, 4H), 3.47 (d, J=10.0 Hz, 1H), 3.39 (d, J=9.9 Hz, 1H), 3.25 (s, 3H), 2.20-0.85 (m), 0.82 (s, 3H); $^{13}$C NMR δ 119.3, 109.2, 71.0, 65.0, 64.5, 64.0, 59.0, 54.0, 50.4, 46.0, 43.8, 38.9, 38.4, 36.2, 34.1, 31.5, 31.1, 31.0 (2×C), 29.6, 28.1, 22.6, 21.7, 14.4. Anal. Calcd for: $C_{24}H_{38}O_5$: C, 70.90%; H, 9.42%. Found: C, 71.17%; H, 9.53%.

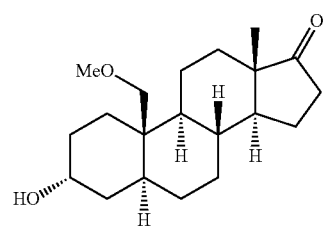

(5α)-19-Methoxyandrostane-3,17-dione (10)

A mixture of steroid 9 (400 mg, 0.98 mmol), PTSA (100 mg), acetone (8 mL) and water (0.5 mL) was stirred at room temperature for 14 h. The reaction was neutralized with aqueous $NaHCO_3$ and the acetone was removed under reduced pressure. Water (80 mL) was added and the product was extracted into EtOAc (60 mL×3). The combined EtOAc extracts were dried and concentrated to give a white solid which was purified by flash column chromatography (silica gel eluted with 20-30% EtOAc in hexanes) to yield product 10 (230 mg, 73%): mp 94-96° C.; IR $v_{max}$ 2918, 1738, 1712, 1452, 1407, 1373, 1270, 1248, 1220, 1202, cm$^{-1}$; $^1$H NMR δ 3.60 (d, J=11.0 Hz, 1H), 3.57 (d, J=11.0 Hz, 1H), 3.26 (s, 3H), 2.50-0.74 (m), 0.82 (s, 3H); $^{13}$C NMR δ 220.5, 211.7, 71.7, 59.0, 53.9, 51.3, 47.6, 46.1, 44.7, 38.9, 38.5, 35.6, 35.3, 34.2, 31.5, 30.3, 28.1, 21.5, 21.3, 13.7. HRMS Calcd for $C_{20}H_{30}O_3$: 318.2195. Found: 318.2180.

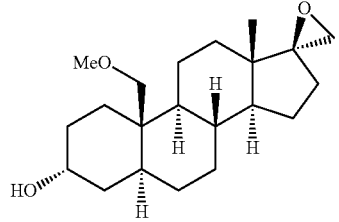

(3α,5α)-3-Hydroxy-19-methoxyandrostan-17-one (11, KK-125)

A 1 M K-Selectride® solution in THF (2 mL, 2 mmol, 3 eq) was added to a cold solution (−78° C.) of steroid 10 (210 mg, 0.66 mmol) in THF (5 mL) and the reaction was stirred at −78° C. for 1.5 h. The reaction was quenched by adding a few drops of acetone and then allowed to warm to room temperature. 3 N aqueous NaOH (10 mL) followed by 30% aqueous $H_2O_2$ (10 mL) was added and the reaction was stirred at room temperature for 1.5 h. The product was extracted into EtOAc (3×60 mL) and the combined EtOAc extracts were washed with brine, dried, and concentrated to give an off-white solid which was purified by flash column chromatography (silica gel eluted with 20-40% EtOAc in hexanes). Product 11 (142 mg, 67%) had: mp 172-174° C.; IR $v_{max}$ 3436, 2921, 1738, 1453, 1406, 1372, 1248, 1203 cm$^{-1}$; $^1$H NMR δ 4.05 (b s, 1H), 3.48 (d, J=9.9 Hz, 1H), 3.38 (d, J=10.2 Hz, 1H), 3.25 (s, 3H), 2.39 (dd, J=19.3, 8.8 Hz, 1H), 2.2.10-0.70 (m), 0.84 (s, 3H); $^{13}$C NMR δ 221.5, 71.1, 66.1, 59.0, 54.6, 51.7, 47.8, 39.6, 39.2, 36.0, 35.7, 35.5, 31.8, 30.7, 29.2, 27.9, 27.1, 21.6, 21.1, 13.8. Anal. Calcd for $C_{20}H_{32}O_3$: C, 74.96%; H, 10.06%. Found: C, 74.91%; H, 9.86%.

(3α,5α,17β)-19-Methoxyspiro[androstane-17,2'-oxiran]-3-ol (12, MQ-90)

To a solution of steroid 11 (100 mg, 0.3 mmol) in DMF (10 mL) was added trimethylsulfonium iodide (306 mg, 1.5 mmol) and potassium tert-butoxide (168 mg, 1.5 mmol) at room temperature. The reaction was quenched by aqueous $NH_4Cl$ after 2 h. The mixture was extracted with dichloromethane (100 mL×2) and washed with brine. The organic layers were combined and dried over MgSO$_4$, filtered, and concentrated. The residue was purified by column chromatography (silica gel eluted with 25% EtOAc in hexanes) to give steroid 12 (76 mg, 75%): mp 168-170° C.; $[\alpha]_D^{20}$=−3.1 (c=0.16, CHCl$_3$); $\nu_{ma}$, 3420, 1445 cm$^{-1}$; $^1$H NMR (CDCl$_3$) δ 4.10-4.05 (m, 1H), 3.51 (d, J=10.2 Hz, 1H), 3.42 (d, J=10.2 Hz, 1H), 3.29 (s, 3H), 2.90 (d, J=5.1 Hz, 1H), 2.60 (d, J=5.0 Hz, 1H), 2.00-0.77 (m), 0.89 (s, 3H); $^{13}$C NMR (CDCl$_3$) δ 71.0, 70.6, 66.4, 59.1, 54.6, 53.6, 53.1, 40.2, 39.6, 39.3, 36.2, 36.1, 34.3, 31.4, 29.4, 29.0, 28.1, 27.1, 23.5, 21.4, 14.4. Anal. Calcd for C$_{21}$H$_{34}$O$_3$: C, 75.41; H, 10.25. Found: C, 75.44; H, 9.98.

(3α,5α)-19-Methoxy-3-(methoxymethoxy)-androstan-17-one (13)

To a solution of steroid 11 (800 mg, 2.5 mmol) in DCM (20 mL) was added chloromethyl methyl ether (302 mg, 3.75 mmol) and N,N-diisopropylethylamine (774 mg, 6 mmol) at room temperature. The mixture was quenched by water after 16 h and extracted with EtOAc (100 mL×2) and washed with brine. The organic layers were dried over with MgSO$_4$, filtered, and concentrated. The residue was purified by column chromatography (silica gel eluted with 25% EtOAc in hexanes) to give product 13 as an oil (900 mg, 100%): IR $\nu_{max}$ 2921, 1740 cm$^{-1}$; $^1$H NMR (CDCl$_3$) δ 4.65

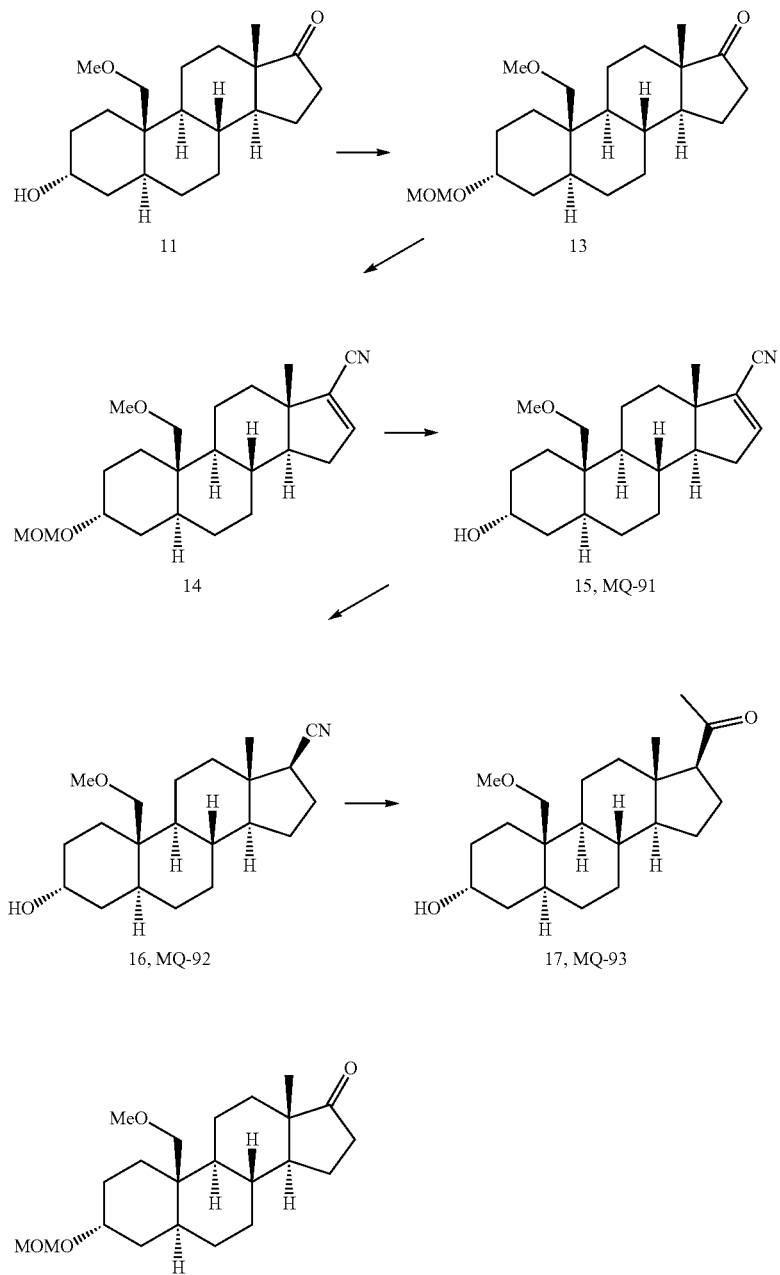

Scheme 4

(q, J=6.6, 10.9, 1H), 3.86-3.84 (m, 1H), 3.52 (d, J=10.2 Hz, 1H), 3.43 (d, J=9.8 Hz, 1H), 3.35 (s, 3H), 3.28 (s, 3H), 2.44-0.83 (m), 0.86 (s, 3H); $^{13}$C NMR (CDCl$_3$) δ 221.4, 94.5, 71.3, 71.2, 59.1, 55.1, 54.6, 51.7, 47.9, 39.9, 39.4, 35.8, 35.5, 34.0, 31.9, 30.8, 28.0, 27.7, 26.5, 21.7, 21.2, 13.9.

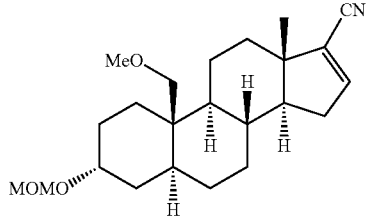

(3α,5α)-19-Methoxy-3-(methoxymethoxy)-androst-16-ene-17-carbonitrile (14)

To a solution of steroid 13 (800 mg, 2.5 mmol) in THF (20 mL) was added potassium bis(trimethylsilyl)amide (3.0 mmol, 0.5 M in toluene, 6.0 mL) at −78° C. After 30 min, N-phenyltrifluoromethanesulfonimide (1.07 g, 3.0 mmol) in 5 mL of THF was added at −78° C. After 2 h at −78° C., the mixture was quenched by water and extracted with EtOAc (50 mL×3). The combined organic layers were dried, filtered, and concentrated. The residue was purified by flash chromatography (silia gel) to afford the intermediate enol triflate (1.21 g containing an inseparable impurity). To the enol triflate (1.21 g) in a 50 mL round flask was added sodium cyanide (300 mg, 6.0 mmol), copper (I) iodide (120 mg, 0.6 mmol) and Pd(PPh$_3$)$_4$ (60 mg) at room temperature. Acetonitrile (25 mL) was added and the mixture was refluxed for 3 h. The mixture was quenched by aqueous NH$_4$Cl and extracted with EtOAc (50 mL×3). The combined organic layers were dried, filtered, and concentrated. The residue was purified by flash column chromatography (silica gel eluted with 10% EtOAc in hexanes) to afford product 14 as an oil (886 mg containing an inseparable impurity): $^1$H NMR (CDCl$_3$) δ 6.54-6.53 (m, 1H), 4.62 (q, J=7.0, 9.8 Hz, 2H), 3.80-3.70 (m, 1H), 3.47 (d, J=9.8 Hz, 1H), 3.39 (d, J=10.2 Hz, 1H), 3.30 (s, 3H), 3.23 (s, 3H), 2.29-0.82 (m), 0.85 (s, 3H); $^{13}$C NMR (CDCl$_3$) δ 147.7, 127.3, 116.0, 94.4, 71.5, 71.3, 59.1, 56.2, 55.0, 54.8, 48.4, 39.9, 39.5, 34.3, 34.2, 33.8, 32.8, 31.6, 27.9, 27.4, 26.4, 21.5, 16.3.

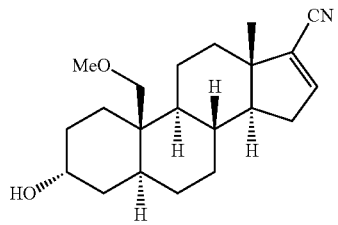

(3α,5α)-3-Hydroxy-19-methoxyandrost-16-ene-17-carbonitrile (15, MQ-91)

To steroid 14 containing an inseparable impurity (886 mg) in methanol (20 mL) was added 6 N HCl (15 ml) at room temperature. After 14 h, the mixture was extracted with dichloromethane (50 mL×2). The combined organic layers were dried, filtered, and concentrated. The residue was purified by flash column chromatography (silica gel eluted with 30% EtOAc in hexanes) to afford product 15 (480 mg, 58% yield from steroid 13): mp 167-169° C.; [α]$_D^{20}$=11.1 (c=0.18, CHCl$_3$); IR v. 3337, 2212 cm$^{-1}$; $^1$H NMR (CDCl$_3$) δ 6.59-6.55 (m, 1H), 4.08-4.05 (m, 1H), 3.53 (d, J=10.1 Hz, 1H), 3.43 (d, J=10.1 Hz, 1H), 3.28 (s, 3H), 2.37-0.89 (m), 0.91 (s, 3H); $^{13}$C NMR (CDCl$_3$) δ 147.2, 127.5, 115.9, 71.1, 66.1, 59.1, 56.2, 54.8, 48.3, 39.7, 39.3, 36.0, 34.4, 34.3, 32.8, 31.6, 29.3, 28.0, 26.9, 21.5, 16.3. Anal. Calcd for C$_{21}$H$_{31}$NO$_2$: C, 76.55; H, 9.48; N, 4.25. Found: C, 76.59; H, 9.32; N, 4.06.

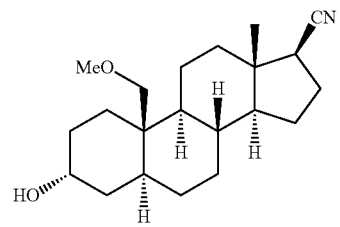

(3α,5α,17β)-3-Hydroxy-19-methoxyandrostane-17-carbonitrile (16, MQ-92)

To a solution of steroid 15 (430 mg, 1.3 mmol) in EtOAc (30 mL) was added Pd/C (10%, 100 mg). A hydrogenation was carried out under 7 atm H$_2$ at room temperature for 3 h. The mixture was filtered through Celite and washed with EtOAc (100 mL). Solvents were removed and the residue was purified by flash column chromatography (silica gel eluted with 10% EtOAc in hexanes) to afford product 16 (415 mg, 96%): mp 146-148° C.; [α]$_D^{20}$=42.1 (c=0.29, CHCl$_3$); v$_{max}$ 3412, 2235 cm$^{-1}$; $^1$H NMR (CDCl$_3$) δ 4.08-4.05 (m, 1H), 3.49 (d, J=9.8 Hz, 1H), 3.39 (d, J=9.8 Hz, 1H), 3.29 (s, 3H), 2.25 (t, J=8.8 Hz, 1H), 2.10-0.79 (m), 0.92 (s, 3H); $^{13}$C NMR (CDCl$_3$) δ 121.4, 70.9, 66.3, 59.1, 54.7, 54.3, 44.5, 40.2, 39.5, 39.2, 37.5, 36.4, 36.1, 31.9, 29.4, 28.0, 27.1, 26.5, 24.5, 21.6, 14.4. Anal. Calcd for C$_{21}$H$_{33}$NO$_2$: C, 76.09; H, 10.03; N, 4.23. Found: C, 76.16; H, 9.90; N, 4.05.

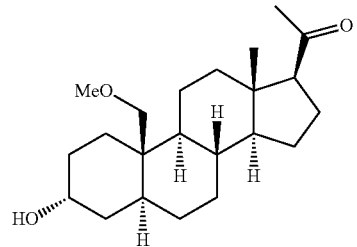

(3α,5α)-3-Hydroxy-19-methoxypregnan-20-one (17, MQ-93)

To a solution of steroid 16 (360 mg, 1.09 mmol) in THF (20 mL) was added methyl magnesiumbromide (3.0 M, 2 mL, 6.0 mmol) at room temperature. The mixture was then refluxed for 16 h and subsequently allowed to cool to room temperature and quenched by 6 N HCl addition. The product was extracted into dichloromethane (50 mL×3). The combined organic layers were dried, filtered, and concentrated. The $^1$H NMR of the crude product (300 mg, 79%) showed the 17β (steroid 17) and 17α diastereomer in the ratio of 8 to 1, respectively. The crude product was purified by flash column chromatography (silica gel eluted with 25% EtOAc in hexanes) to afford pure product 17 (135 mg) pure: mp 160-162° C.; [α]$_D^{20}$=41.7 (c=0.31, CHCl$_3$); IR v$_{max}$ 3407, 1703 cm$^{-1}$; $^1$H NMR (CDCl$_3$) δ 4.07-4.05 (m, 1H), 3.47 (d, J=9.8 Hz, 1H), 3.40 (d, J=10.2 Hz, 1H), 3.26 (s, 3H), 2.50 (t, J=9.4 Hz, 1H), 2.17-0.78 (m), 2.08 (s, 3H), 0.59 (s, 3H); $^{13}$C NMR (CDCl$_3$) δ 209.8, 70.9, 66.3, 63.8, 59.0, 56.9, 54.4, 44.3, 39.5, 39.4, 39.2, 36.1, 35.9, 31.8, 31.4, 29.3, 28.1, 26.9, 24.3, 22.6, 22.0, 13.5. Anal. Calcd for C$_{22}$H$_{36}$O$_3$: C, 75.82; H, 10.41. found: C, 75.71; H, 10.29.

Scheme 5

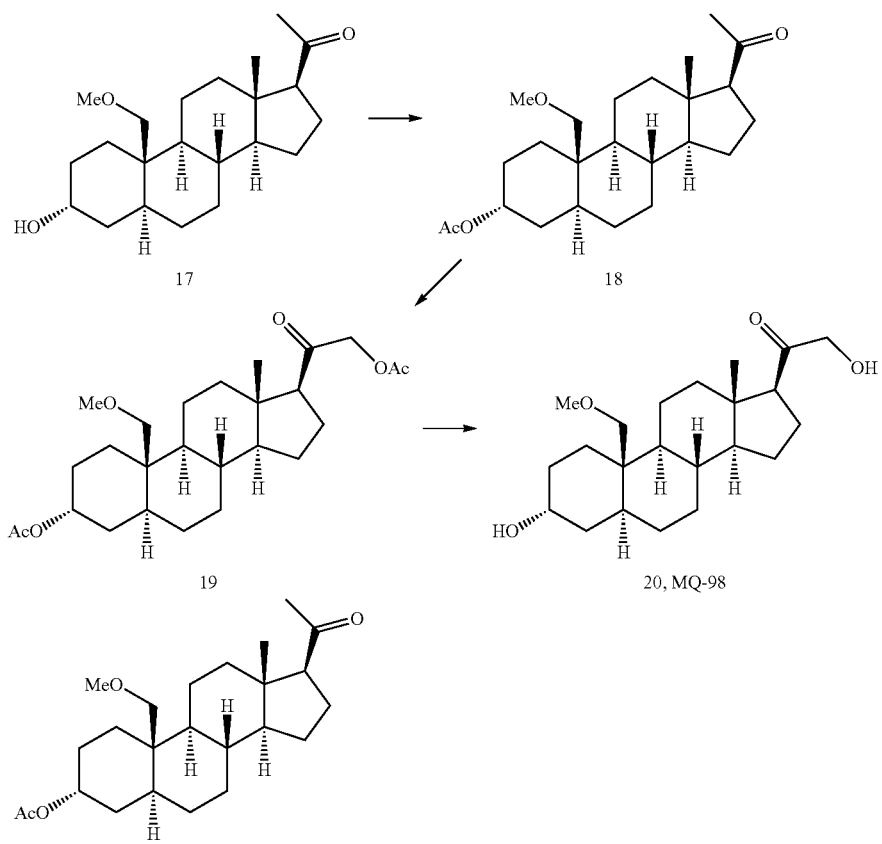

(3α,5α)-3-(Acetyloxy)-19-methoxypregnan-20-one (18)

To a solution of steroid 17 (100 mg, 0.29 mmol) in pyridine (5 mL) was added acetic anhydride (51 mg, 0.5 mmol) and DMAP (5 mg) at room temperature. The reaction mixture was quenched by water after 2 h and extracted with EtOAc (50 mL×2). The combined organic layers were dried with MgSO$_4$, filtered, and concentrated. The residue was purified by flash column chromatography (silica gel eluted with 20% EtOAc in hexanes) to give product 18 as an oil (112 mg, 100%): $^1$H NMR (CDCl$_3$) δ 5.01-4.98 (m, 1H), 3.46 (d, J=9.8 Hz, 1H), 3.37 (d, J=9.8 Hz, 1H), 3.23 (s, 3H), 2.47 (t, J=9.0 Hz, 1H), 2.22-0.79 (m), 2.06 (s, 3H), 2.00 (s, 3H), 0.57 (s, 3H); $^{13}$C NMR (CDCl$_3$) δ 209.4, 170.5, 70.9, 69.9, 63.7, 59.0, 56.8, 54.2, 44.2, 40.1, 39.3, 39.1, 35.8, 33.1, 31.7, 31.4, 27.8, 27.7, 26.3, 24.2, 22.6, 21.9, 21.4, 13.4.

(3α,5α)-3,21-bis(Acetyloxy)-19-methoxylpregnan-20-one (19)

To a solution of steroid 18 (112 mg, 0.29 mmol) in benzene (10 mL) and methanol (0.5 mL) was added lead tetraacetate (513 mg, 1.15 mmol) and boron trifluoride ether complex (1 mL) at room temperature. After 3 h, water was added and the product extracted into EtOAc (50 mL×2). The combined organic layers were dried over with MgSO$_4$, filtered, and concentrated. The residue was purified by flash column chromatography (silica gel eluted with 25% EtOAc in hexanes) to give product 19 as a foam (82 mg, 63%): $^1$H NMR (CDCl$_3$) δ 5.03-5.01 (m, 1H), 4.70 (d, J=16.8 Hz, 1H), 4.53 (d, J=16.8 Hz, 1H), 3.47 (d, J=10.2 Hz, 1H), 3.34 (d, J=10.2 Hz, 1H), 3.25 (s, 3H), 2.47 (t, J=9.0 Hz, 1H), 2.20-0.80 (m), 2.14 (s, 3H), 2.03 (s, 3H), 0.65 (s, 3H); $^{13}$C NMR (CDCl$_3$) δ 203.8, 170.6, 170.2, 70.9, 69.9, 69.1, 59.4, 59.0, 57.1, 54.2, 45.0, 40.1, 39.2, 39.1, 35.9, 33.2, 31.8, 27.9, 27.8, 26.4, 24.4, 22.7, 22.0, 21.5, 20.4, 13.3.

(3α,5α)-3,21-Dihydroxy-19-methoxypregnan-20-one (20, MQ-98)

To a solution of steroid 19 (82 mg, 0.18 mmol) in methanol was added potassium bicarbonate (280 mg, 2.0 mmol) at room temperature. The mixture was refluxed for 5 h. Water was added and the product was extracted into EtOAc (50 mL×2). The combined organic layers were dried over with MgSO$_4$, filtered, and concentrated. The residue was purified by flash column chromatography (silica gel eluted with 25% EtOAc in hexanes) to give product 20 (22 mg, 37%): mp 88-90° C.; [α]$_D^{20}$=50.0 (c=0.13, CHCl$_3$); IR ν$_{max}$ 3415, 1708 cm$^{-1}$; $^1$H NMR (CDCl$_3$) δ 4.20-4.10 (m, 3H), 3.49 (d, J=9.8 Hz, 1H), 3.42 (d, J=9.8 Hz, 1H), 3.28 (d, J=1.9 Hz, 3H), 2.47 (t, J=8.6 Hz, 1H), 2.22-0.80 (m), 0.65 (J=1.2 Hz, 3H); $^{13}$C NMR (CDCl$_3$) δ 210.4, 70.9, 69.4, 66.4, 59.4, 59.1, 57.1, 54.3, 45.1, 39.5, 39.2, 39.1, 36.1, 36.0, 31.9, 29.4, 28.1, 27.0, 24.5, 22.9, 22.0, 13.6. Anal. Calcd for C$_{22}$H$_{36}$O$_4$: C, 72.49; H, 9.95. found: C, 72.77; H, 10.10.

Scheme 6

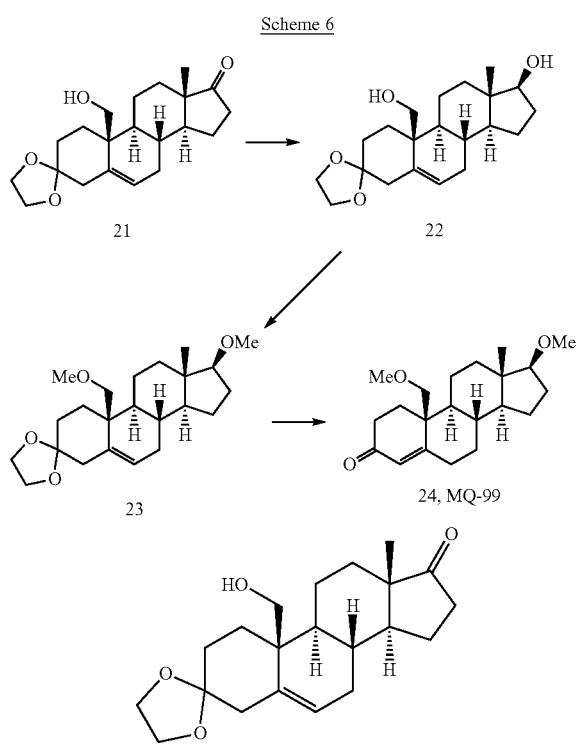

19-Hydroxyandrost-5-ene-3,17-dione, 3-cyclic 1,2-ethandiyl acetal (21)

To a solution of the known 19-hydroxyandrost-4-ene-3,17-dione (1.0 g, 3.3 mmol) in benzene (100 mL) was added ethylene glycol (267 mg, 4.3 mmol) and PPTS (100 mg). The mixture was refluxed in a flask equipped with a Dean-Stark trap. After 4 h, the mixture was cooled down to room temperature and solvent was removed by reduced pressure. The residue was purified by flash column chromatography (silica gel eluted with 15% EtOAc in hexanes) to afford the known 19-hydroxyandrost-5-ene-3,17-dione, 3,17-bis(cyclic 1,2-ethandiyl acetal) (260 mg, 20%) and product 21 (450 mg, 39%): mp 190-192° C.; IR ν$_{max}$ 3468, 1735 cm$^{-1}$; $^1$H NMR (CDCl$_3$) δ 5.67-5.65 (m, 1H), 3.93-3.3.77 (m, 5H), 3.58-3.55 (m, 1H), 2.48-0.96 (m), 0.87 (s, 3H); $^{13}$C NMR (CDCl$_3$) δ 221.2, 135.4, 126.4, 109.0, 64.4, 64.2, 62.5, 52.4, 50.0, 47.8, 41.8, 41.6, 35.7, 32.8, 32.4, 31.6, 31.3, 30.0, 21.7, 20.9, 13.9.

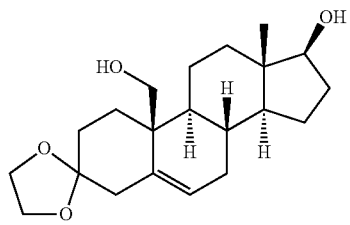

(17β)-17,19-Dihydroxyandrost-5-en-3-one, 3-cyclic 1,2-ethandiyl acetal (22)

To a solution of steroid 21 (450 mg, 1.29 mmol) in ethanol (50 mL) was added sodium borohydride (152 mg, 4 mmol) at room temperature. After 3 h, aqueous NH$_4$Cl was added and the product extracted into EtOAc (50 mL×3). The combined organic layers were dried with MgSO$_4$, filtered, and concentrated. The residue was purified by flash column chromatography (silica gel eluted with 35% EtOAc in hexanes) to give product 22 (374 mg, 83%): mp 208-210° C.; IR ν$_{max}$ 3440 cm$^{-1}$; $^1$H NMR (CDCl$_3$) δ 5.74-5.70 (m, 1H), 4.00-3.92 (m, 4H), 3.85 (d, J=11.4 Hz, 1H), 3.70-3.62 (m, 2H), 2.22-0.84 (m), 0.82 (s, 3H); $^{13}$C NMR (CDCl$_3$) δ 135.1, 127.3, 109.1, 81.8, 64.5, 64.3, 62.6, 52.1, 50.0, 42.9, 41.9, 41.8, 36.8, 33.4, 32.4, 31.4, 30.6, 30.5, 23.3, 21.3, 11.3.

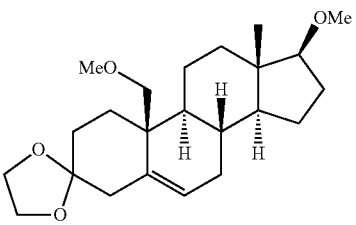

(17β)-17,19-Dimethoxyandrost-5-en-3-one, 3-cyclic 1,2-ethandiyl acetal (23)

To a solution of steroid 22 (374 mg, 0.72 mmol) in THF (30 mL) was added sodium hydride (400 mg, 60% in mineral oil, 6.0 mmol). After addition, the mixture was refluxed for 1 h, iodomethane (2.13 g, 15 mmol) was added and reflux was continued for 3 h. After allowing cooling to room temperature, water was added and the product was extracted into EtOAc (100 mL×3). The combined organic layers were dried with MgSO$_4$, filtered, and concentrated. The residue was purified by flash column chromatography (silica gel eluted with 20% EtOAc in hexanes) to give product 22 (402 mg, 100%): mp 97-99° C.; IR ν$_{max}$ 2918, 1450, 1105 cm$^{-1}$; $^1$H NMR (CDCl$_3$) δ 5.52-5.50 (m, 1H), 3.95-3.83 (m, 4H), 3.51 (d, J=9.8 Hz, 1H), 3.27 (s, 3H), 3.27 (d, J=11.4 Hz, 1H), 3.24 (s, 3H), 3.15 (t, J=7.8 Hz, 1H), 2.56-0.78 (m), 0.73 (s, 3H); $^{13}$C NMR (CDCl$_3$) δ 136.1, 124.8, 109.1, 90.6, 73.6, 64.2, 64.0, 58.8, 57.6, 51.9, 49.9, 42.6, 42.0, 40.6, 38.0, 32.6, 32.5, 31.3, 30.8, 27.5, 23.1, 21.2, 11.3.

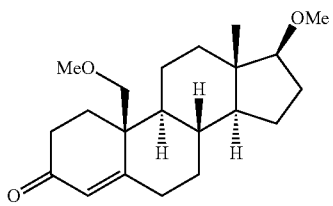

(17β)-17,19-Dimethoxyandrost-4-en-3-one (24, MQ-99)

To a solution of steroid 23 (402 mg, 1.07 mmol) in THF (20 mL) was added 3 N HCl (10 mL at room temperature. The mixture was stirred for 2 h and the product extracted into dichloromethane (50 mL×2). The combined organic layers were dried with MgSO$_4$, filtered, and concentrated. The residue was purified by flash column chromatography (silica gel eluted with 25% EtOAc in hexanes) to give product 24 (355 mg, 100%): IR $v_{max}$ 1671 cm$^{-1}$; mp 93-95° C.; $[\alpha]_D^{20}$=124.7 (c=0.32, CHCl$_3$); $^1$H NMR (CDCl$_3$) δ 5.80 (d, J=0.7 Hz, 1H), 3.68 (d, J=9.3 Hz, 1H), 3.51 (d, J=9.4 Hz, 1H), 3.28 (s, 3H), 3.25 (s, 3H), 3.18 (t, J=8.2 Hz, 1H), 2.27-0.90 (m), 0.74 (s, 3H); $^{13}$C NMR (CDCl$_3$) δ 199.9, 167.5, 125.5, 90.2, 76.0, 59.2, 57.7, 54.1, 50.9, 42.8, 42.7, 37.8, 35.9, 34.8, 33.6, 33.4, 31.6, 27.4, 23.0, 21.2, 11.5. Anal. Calcd for C$_{21}$H$_{32}$NO$_3$: C, 75.86; H, 9.70. Found: C, 76.00; H, 9.98.

Scheme 7

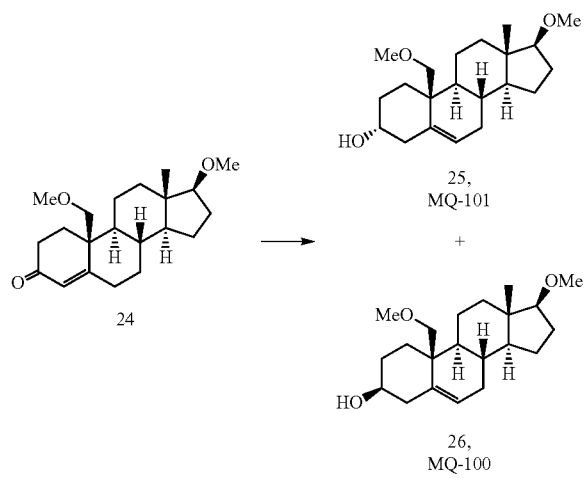

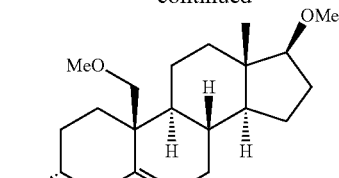

25, MQ-101 and

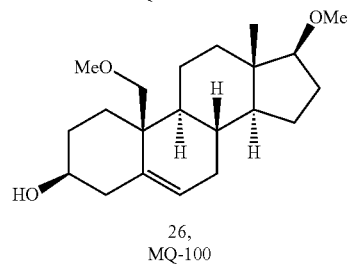

26, MQ-100

(3α,17β)-17,19-Dimethoxyandrost-5-en-3-ol (25, MQ-101) and (3β,17β)-17,19-Dimethoxyandrost-5-en-3-ol (26, MQ-100)

To a solution of steroid 24 (355 mg, 1.07 mmol) in acetic anhydride (10 mL) was added sodium iodide (600 mg, 4 mmol) and TMSCl (435 mg, 4 mmol) at 0° C. After addition, the mixture was allowed to warm up to room temperature for 1 h. Thin layer chromatography showed no remaining starting material. Aqueous NaHCO$_3$ was added and the product extracted into EtOAc (50 mL×3). The combined organic layers were dried with MgSO$_4$, filtered, and concentrated. The residue was dissolved in ethanol (20 mL) and NaBH$_4$ (200 mg) was added. After 16 h, aqueous NH$_4$Cl was added and the product extracted into EtOAc (50 mL×3). The combined organic layers were dried with MgSO$_4$, filtered, and concentrated. The residue was purified by flash column chromatography (silica gel eluted with 30% EtOAc in hexanes) to give product 25 (30 mg, 8%), and product 26 (248 mg, 69%).

Product 25 had: mp 132-134° C.; $[\alpha]_D^{20}$=−64.0 (c=0.10, CHCl$_3$); IR $v_{max}$ 3337, 1446 cm$^{-1}$; $^1$H NMR (CDCl$_3$) δ 5.67-5.65 (m, 1H), 4.05-4.00 (m, 1H), 3.60 (d, J=9.8 Hz, 1H), 3.35 (s, 3H), 3.31 (s, 3H), 3.28 (d, J=9.8 Hz, 1H), 3.25 (t, J=8.2 Hz, 1H), 2.64-2.60 (m, 1H), 2.17-0.85 (m), 0.80 (s, 3H); $^{13}$C NMR (CDCl$_3$) δ 134.8, 126.9, 90.8, 73.7, 66.9, 59.1, 57.9, 52.1, 50.8, 42.8, 41.5, 40.0, 38.2, 32.9, 31.1, 30.2, 29.3, 27.7, 23.3, 21.1, 11.5. Anal. Calcd for C$_{21}$H$_{34}$O$_3$: C, 75.41; H, 10.25. Found: C, 75.31; H, 10.41.

Product 26 had: mp 160-162° C.; $[\alpha]_D^{20}$=−76.7 (c=0.45, CHCl$_3$); IR $v_{max}$ 3408 cm$^{-1}$; $^1$H NMR (CDCl$_3$) δ 5.53-5.50 (m, 1H), 3.54 (d, J=9.7 Hz, 1H), 3.51-3.44 (m, 1H), 3.28 (s, 3H), 3.24 (s, 3H), 3.22 (d, J=9.7 Hz, 1H), 3.18 (t, J=8.2 Hz, 1H), 2.65 (s, br, 1H), 2.32-0.76 (m), 0.73 (s, 3H); $^{13}$C NMR (CDCl$_3$) δ 136.9, 124.4, 90.7, 73.8, 71.1, 58.8, 57.7, 51.9, 50.4, 42.6, 42.2, 40.5, 38.0, 33.6, 32.6, 31.6, 30.7, 27.5, 23.1, 21.2, 11.3. Anal. Calcd for C$_{21}$H$_{34}$O$_3$: C, 75.41; H, 10.25. Found: C, 75.51; H, 10.30.

Scheme 8

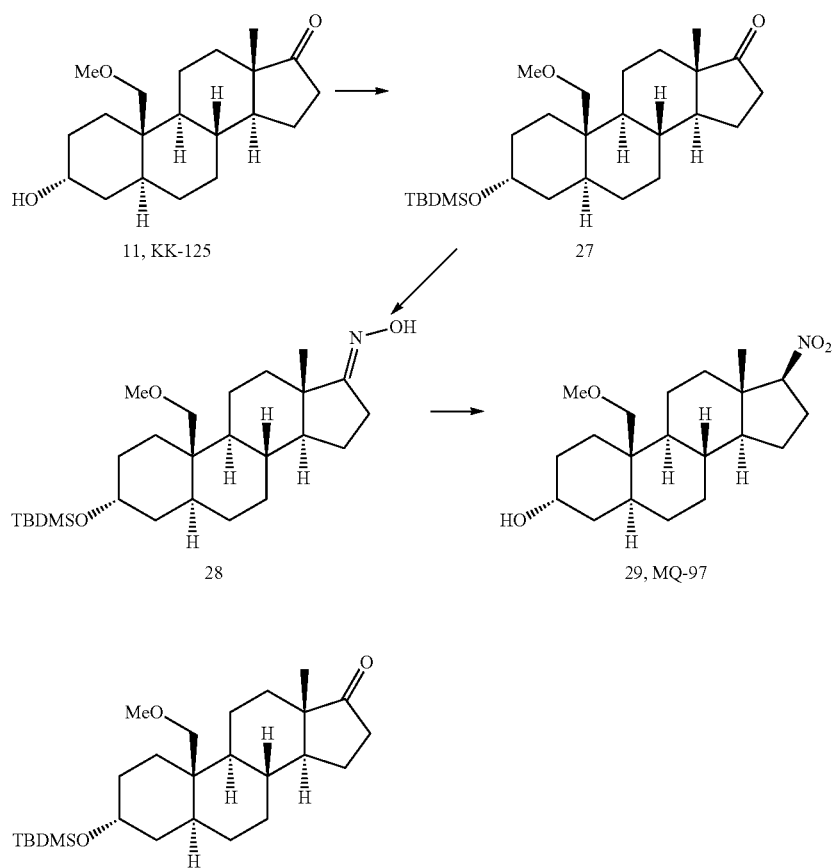

(3α,5α)-3-[[(Dimethylethyl)dimethylsilyl]oxy]-19-methkoxyandrostan-17on (27)

To a solution of steroid 11 (150 mg, 0.47 mmol) in DMF (5 ml) was added tert-butyldimethylsilyl chloride (150 mg, 1.0 mmol) and imidazole (132 mg, 2.0 mmol) at room temperature. After 16 h, water was added and the product extracted into EtOAc (50 mL×2). The combined organic layers were dried with MgSO$_4$, filtered and removed. The residue was purified by flash column chromatography (silica gel eluted with 10% EtOAc in hexanes) to afford product 27 as an oil (198 mg, 99%): $^1$H NMR (CDCl$_3$) δ 4.00-3.95 (m, 1H), 3.51 (d, J=9.7 Hz, 1H), 3.40 (d, J=9.7 Hz, 1H), 3.27 (s, 3H), 2.44-0.80 (m), 0.89 (s, 3H), 0.87 (s, 9H), 0.00 (d, J=1.6 Hz, 6H); $^{13}$C NMR (CDCl$_3$) δ 221.6, 71.3, 66.6, 59.1, 54.7, 51.7, 47.9, 39.6, 39.2, 37.0, 35.8, 35.5, 31.8, 30.9, 29.9. 28.1, 27.2, 25.8 (3×C), 25.6, 21.7, 21.2, 13.9, −4.90, −4.92.

(3α,5α)-3-[[(Dimethylethyl)dimethylsilyl]oxy]-19-methoxyandrostan-17-one, oxime (28)

To a solution of the steroid 27 (195 mg, 0.45 mmol) in pyridine (10 mL) was added hydroxyamine hydrochloride (140 mg, 2.0 mmol) at room temperature. After 14 h, water was added and the product extracted into EtOAc (50 mL×2). The combined organic layers were dried with MgSO$_4$, filtered and removed. The residue was purified by flash column chromatography (silica gel eluted with 20% EtOAc in hexanes) to afford product 28 as an oil (202 mg, 100%): $^1$H NMR (CDCl$_3$) δ 9.05 (s, br, 1H), 4.00-3.95 (m, 1H), 3.50 (d, J=9.8 Hz, 1H), 3.41 (d, J=9.8 Hz, 1H), 3.27 (s, 3H), 2.50-0.82 (m), 0.91 (s, 3H), 0.88 (s, 9H), 0.11 (d, J=1.9 Hz, 6H); $^{13}$C NMR (CDCl$_3$) δ 171.1, 71.4, 66.7, 59.1, 54.7, 54.1, 44.2, 39.6, 39.2, 37.1, 35.2, 34.3, 31.5, 30.0, 28.2, 27.1, 25.8 (3×C), 25.0, 23.1, 21.5, 18.1, 17.2, −4.85, −4.89.

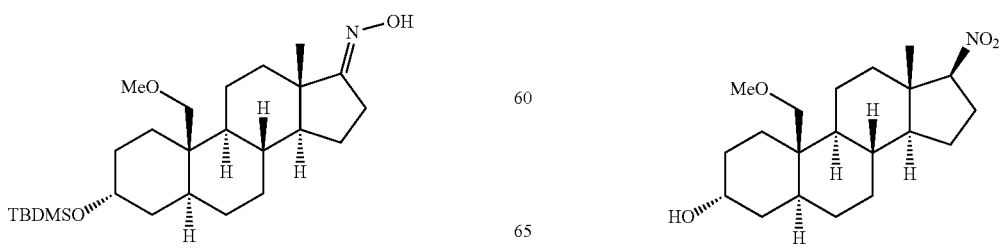

(3α,5α,17β)-19-methoxy-17-nitroandrostan-3-ol
(29, MQ-97)

To a solution of NBS (231 mg, 1.3 mmol) in dioxane (4 mL) was added aqueous KHCO$_3$ (260 mg, 2.6 mmol, 4 mL) at room temperature. The mixture was stirred for 30 min at room temperature, then the oxime (202 mg, 0.45 mmol) in dioxane (10 ml) was added. The reaction was stirred in an open flask for 14 h at room temperature. NaBH$_4$ was added (200 mg) in 5 portions and the reaction was stirred for 3 h at room temperature. 6 N HCl (10 ml) was slowly added and stirring at room temperature was continued for 1 h. The product was extracted into dichloromethane (50 mL×2). The combined organic layers were dried with MgSO$_4$, filtered, and removed. The residue was purified by flash column chromatography (silica gel eluted with 30% EtOAc in hexanes) to afford product 29 (79 mg, 50%): mp 52-54° C.; $[\alpha]_D^{20}$=25.8 (c=0.21, CHCl$_3$); IR $\nu_{max}$ 3307, 1541, 1370 cm$^{-1}$; $^1$H NMR (CDCl$_3$) δ 4.38 (t, J=8.6 Hz, 1H), 4.10-4.05 (m, 1H), 3.49 (d, J=9.8 Hz, 1H), 3.41 (d, J=9.8 Hz, 1H), 3.27 (s, 3H), 2.55-0.79 (m), 0.74 (s, 3H); $^{13}$C NMR (CDCl$_3$) δ 94.5, 71.0, 66.3, 59.1, 54.2, 53.4, 46.0, 39.5, 39.1, 37.6, 36.0, 31.5, 29.3, 28.0, 27.1, 24.7, 23.6, 21.7, 12.2. Anal. Calcd for C$_{20}$H$_{33}$NO$_4$: C, 68.34; H, 9.46. Found: C, 68.40; H, 9.45.

mL×2) and washed with brine. The combined organic extracts were dried with MgSO$_4$, filtered, and concentrated. The residue was purified by flash column chromatography (silica gel eluted with 30% EtOAc in hexanes) to give product 30 (239 mg, 81%): mp 208-210° C.; IR $\nu_{max}$ 3428, 1737, 1642 cm$^{-1}$; $[\alpha]_D^{20}$=−81.3 (c=0.31, CHCl$_3$); $^1$H NMR (CDCl$_3$) δ 3.65-3.58 (m, 1H), 3.52 (d, J=9.8 Hz, 1H), 3.43 (d, J=9.8 Hz, 1H), 3.27 (s, 3H), 2.44-0.65 (m), 0.85 (s, 3H); $^{13}$C NMR (CDCl$_3$) δ 221.4, 71.5, 70.8, 59.1, 54.6, 51.6, 47.9, 44.9, 39.0, 38.3, 35.8, 35.5, 32.0, 31.8, 31.6, 30.8, 28.0, 21.7, 21.6, 13.8. Anal. Calcd for C$_{20}$H$_{32}$O$_3$: C, 74.96; H, 10.06. Found: C, 75.10; H, 9.95.

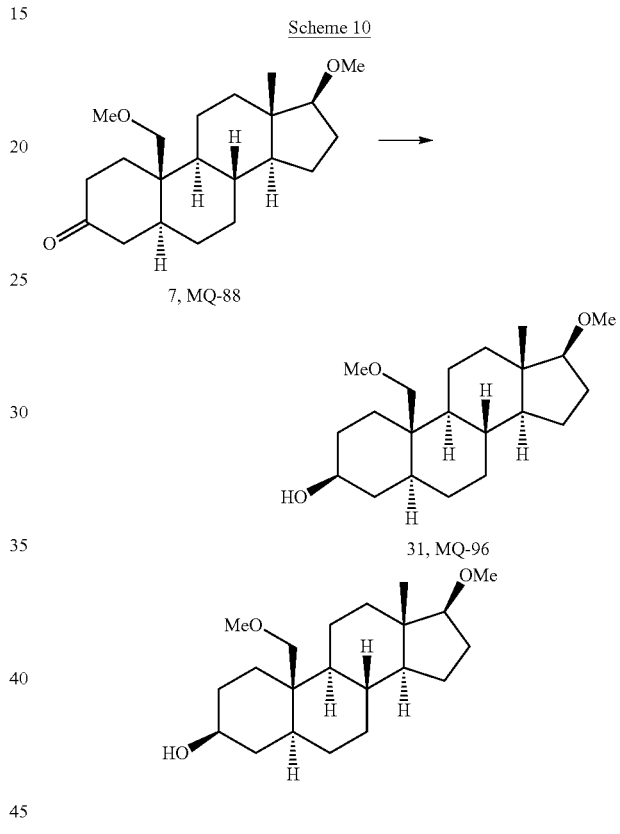

Scheme 10

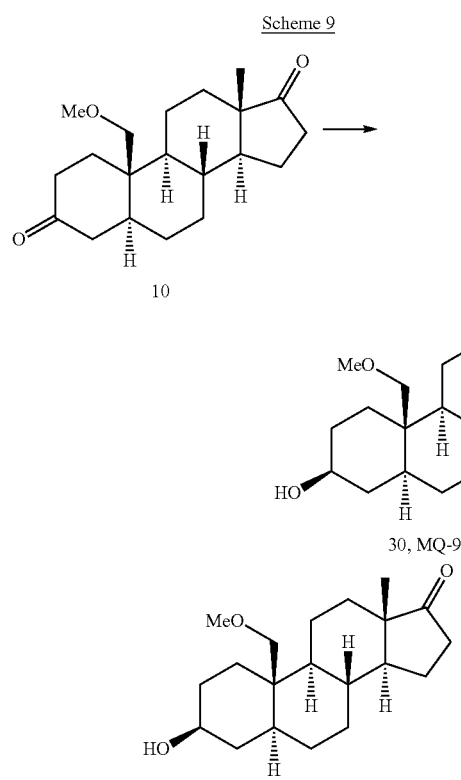

Scheme 9

(3α,5β)-3-Hydroxy-19-methoxyandrostan-17-one
(30, MQ-94)

To a solution of steroid 10 (295 mg, 0.93 mmol) in THF (20 mL) was added lithium aluminum tri-tert-butoxide hydride (2.0 mmol, 1.0 M in THF, 2.0 mL) at −40° C. After 2 h, the mixture was quenched by 3 N HCl at −40° C., the reaction was allowed to warm up to room temperature for 1 h. The product was extracted into dichloromethane (100

(3β,5α,17β)-17,19-Dimethoxyandrostan-3-ol (31, MQ-96)

To a solution of steroid 7 (65 mg, 0.20 mmol) in THF (10 mL) was added lithium aluminum tri-tert-butoxide hydride (1.0 mmol, 1.0 M in THF, 1.0 mL) at −40° C. After 2 h, the mixture was quenched by 3 N HCl at −40° C. and the reaction was allowed to warm up to room temperature for 1 h. The product was extracted into dichloromethane (50 mL×2) and washed with brine. The combined organic layers were dried with MgSO$_4$, filtered, and concentrated. The residue was purified by flash column chromatography (silica gel eluted with 25% EtOAc in hexanes) to give product 31 (55 mg, 85%): mp 164-166° C.; IR $\nu_{max}$ 3370 cm$^{-1}$; $[\alpha]_D^{20}$=1.0 (c=0.10, CHCl$_3$); $^1$H NMR (CDCl$_3$) δ 3.65-3.57 (m, 1H), 3.51 (d, J=10.2 Hz, 1H), 3.43 (d, J=10.2 Hz, 1H), 3.33 (s, 3H), 3.29 (s, 3H), 3.22 (t, J=8.2 Hz, 1H), 2.24-0.60 (m), 0.76 (s, 3H); $^{13}$C NMR (CDCl$_3$) δ 90.8, 71.5, 71.0, 59.1, 57.8, 54.7, 51.5, 45.0, 43.0, 38.9, 38.5, 38.4, 35.8, 32.0, 31.8, 31.6, 28.2, 27.7, 23.2, 22.2, 11.7. Anal. Calcd for C$_{21}$H$_{36}$O$_3$: C, 74.95; H, 10.78. Found: C, 74.91; H, 10.82.

B. [$^{35}$S]-TBPS Displacement

The IC$_{50}$ values for non-competitive displacers of [$^{35}$S]-TBPS from the picrotoxin binding site on GABA$_A$ receptors are reported in Table 1.

TABLE 1

Inhibition of [$^{35}$S]-TBPS Binding by Example Compounds[a]

| Compound | IC$_{50}$ (nM) | n$_{Hill}$ |
|---|---|---|
| 7, MQ-88 (Prodrug) | 8,700 ± 1,500 | 1.27 ± 0.15 |
| 8, MQ-89 | 56 ± 2 | 1.05 ± 0.03 |
| 10 (Prodrug) | — | — |
| 11, KK-125 | 4,300 ± 1,200 | 0.95 ± 0.15 |
| 12, MQ-90 | 79 ± 4 | 1.06 ± 0.04 |
| 15, MQ-91 | 118 ± 13 | 1.01 ± 0.10 |
| 16, MQ-92 | 63 ± 7 | 1.24 ± 0.14 |
| 17, MQ-93 | 47 ± 4 | 1.17 ± 0.09 |
| 20, MQ-98 | 345 ± 61 | 0.88 ± 0.12 |
| 24, MQ-99 (Prodrug) | 14,500 ± 10,700 | 1.24 ± 0.47 |
| 25, MQ-101 | 583 ± 71 | 0.94 ± 0.09 |
| 26, MQ-100 (Prodrug) | 17,800 ± 8,400 | 1.19 ± 0.24 |
| 29, MQ-97 | 37 ± 4 | 0.88 ± 0.08 |
| 30, MQ-94 (Prodrug) | >30,000 | — |
| 31, MQ-96 (Prodrug) | 7,800 ± 2,900 | 1.27 ± 0.33 |

[a]Results presented are from duplicate experiments performed in triplicate. Error limits are calculated as standard error of the mean. Methods used are known in the art (see Jiang, X., et al., Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5α)-3-hydroxypregnan-20-one. J. Med. Chem., 46: 5334-48 (2003) - the contents of which are hereby incorporated by reference in their entirety).

C. Electrophysiology Results

The compounds of the present disclosure were evaluated for the ability to potentiate chloride currents mediated by 2 µM GABA at rat α$_1$β$_2$γ$_{2L}$ type GABA$_A$ receptors expressed in *Xenopus laevis* oocytes and the results are shown in Table 2.

TABLE 2

Modulation of Rat α$_1$β$_2$γ$_{2L}$ GABA$_A$ Receptor Function by Example Compounds

| | oocyte electrophysiology[a] | | | |
|---|---|---|---|---|
| Compound | 0.1 µM | 1 µM | 10 µM | (gating) 10 µM |
| 7, MQ-88 (Prodrug) | 1.00 ± 0 | 0.85 ± 0.01 | 1.07 ± 0.02 | 0.04 ± 0.03 |
| 8, MQ-89 | 1.65 ± 0.08 | 7.63 ± 0.77 | 20.9 ± 2.73 | 0.22 ± 0.01 |
| 10 (Prodrug) | — | — | — | — |
| 11, KK-125 | 0.71 ± 0.02 | 0.76 ± 0.07 | 2.17 ± 0.12 | 0 ± 0.07 |
| 12, MQ-90 | 1.24 ± 0.05 | 7.40 ± 1.43 | 18.7 ± 6.19 | 0.14 ± 0.04 |
| 15, MQ-91 | 1.27 ± 0.13 | 5.34 ± 0.86 | 25.6 ± 3.23 | 0.10 ± 0.09 |
| 16, MQ-92 | 1.52 ± 0.02 | 9.79 ± 0.53 | 25.7 ± 2.11 | 0.25 ± 0.11 |
| 17, MQ-93 | 2.15 ± 0.19 | 12.8 ± 1.74 | 33.8 ± 5.44 | 0.23 ± 0.07 |
| 20, MQ-98 | 0.98 ± 0.01 | 2.76 ± 0.27 | 19.0 ± 2.31 | 0.09 ± 0.05 |
| 24, MQ-99 (Prodrug) | 0.88 ± 0.08 | 0.63 ± 0.06 | 1.06 ± 0.17 | 0.11 ± 0.17 |
| 25, MQ-101 | 0.94 ± 0.07 | 1.97 ± 0.08 | 15.7 ± 0.90 | 0.08 ± 0.07 |
| 26, MQ-100 (Prodrug) | 0.83 ± 0.03 | 0.76 ± 0.02 | 0.78 ± 0.02 | 0.02 ± 0.02 |
| 29, MQ-97 | 2.07 ± 0.09 | 15.7 ± 1.45 | 26.6 ± 4.34 | 0.11 ± 0.01 |
| 30, MQ-94 (Prodrug) | 0.90 ± 0.02 | 0.88 ± 0.01 | 0.84 ± 0.02 | 0.03 0.02 |
| 31, MQ-96 (Prodrug) | 0.91 ± 0.02 | 0.97 ± 0.05 | 1.10 ± 0.05 | 0.02 ± 0 |

[a]The GABA concentration used for the control response was 2 µM. Each compound was evaluated on at least four different oocytes at the concentrations indicated, and the results reported are the ratio of currents measured in the presence/absence of added compound. Gating represents direct current gated by 10 µM compound in the absence of GABA, and this current is reported as the ratio of compound only current/2 µM GABA current. Error limits are calculated as standard error of the mean (N ≥ 4). Methods used are known in the art (see Jiang, X., et al.).

D. Tadpole Loss of Righting and Swimming

Table 3 discloses the anesthetic effects of the compounds of the present disclosure. In particular, the anesthetic effect of the compounds of the present disclosure on Loss of Righting Reflex (LRR) and Loss of Swimming Reflex (LSR).

TABLE 3

Effects of Examples on Tadpole Righting and Swimming Reflexes[a]

| Compound | Tadpole LRR EC$_{50}$ (µM) | Tadpole LRR n$_{Hill}$ | Tadpole LSR EC$_{50}$ (µM) | Tadpole LSR n$_{Hill}$ |
|---|---|---|---|---|
| 7, MQ-88 (Prodrug) | 1.71 ± 0.25 | −2.41 ± 0.56 | 5.48 ± 0.12 | −33.3 ± 0.10 |
| 8, MQ-89 | 332 ± 43 | −2.32 ± 0.75 | 1.07 ± 0.01 | −16.1 ± 0.64 |
| 10 (Prodrug) | — | — | — | — |
| 11, KK-125 | 7.95 ± 3.29 | −1.81 ± 0.97 | 17.3 ± 0.2 | −36.2 ± 0.2 |
| 12, MQ-90 | 1.73 ± 0.05 | −2.53 ± 0.11 | 3.54 ± 2.33 | −17.9 ± 71 |
| 15, MQ-91 | 1.22 ± 0.94 | −7.11 ± 28.0 | 2.71 ± 0 | −21.4 ± 0.7 |
| 16, MQ-92 | 0.36 ± 0.04 | −3.37 ± 1.34 | 0.99 ± 0.17 | −21.7 ± 0.6 |
| 17, MQ-93 | 0.36 ± 0.04 | −2.74 ± 1.12 | 1.71 ± 0.03 | −36.3 ± 0.1 |
| 20, MQ-98 | 3.15 ± 0.50 | −2.54 ± 1.23 | 5.48 ± 0.12 | −33.3 ± 0.1 |
| 24, MQ-99 (Prodrug) | None | — | None | — |
| 25, MQ-101 | 3.38 ± 0.38 | −2.80 ± 1.13 | 10.5 ± 0 | −21.1 ± 0 |
| 26, MQ-100 (Prodrug) | None | — | None | — |
| 29, MQ-97 | 0.16 ± 0.01 | −1.84 ± 0.11 | 0.55 ± 0.01 | −33.3 ± 0.1 |
| 30, MQ-94 (Prodrug) | >10 | — | None | — |
| 31, MQ-96 (Prodrug) | 7.04 ± 1.98 | −1.66 ± 0.51 | 16.8 ± 5.9 | −3.27 ± 2.5 |

Methods used are known in the art (see Jiang, X., et al.). Error limits are calculated as standard error of the mean (N=10 or more animals at each of five or more different concentrations).

E. Rat Loss of Righting Reflex

The plasma pharmacokinetics and a qualitative assessment of sedation were obtained in male Sprague Dawley rats according to the following procedure. Rats were dosed by intravenous bolus dose (60 seconds) via the foot dorsal vein at doses ranging from 5 to 15 mg/kg in an appropriate vehicle. In order to assess sedation, rats were gently restrained by hand to a lateral position for dose administration. If decreased muscle tone was observed during dose administration, restraint was gradually reduced. If the animal was unable to return to an upright position, the time was recorded as the onset of loss of righting reflex (LRR). In the event that LRR did not occur during dosing, the animals were evaluated at 5 minute intervals thereafter by being placed in dorsal recumbency. Sluggish or incomplete righting twice consecutively within a 30 second interval qualifies as a loss of righting reflex. After onset of LRR, animals were assessed every 5 minutes in the same manner. Recovery of righting reflex is defined as the ability of a rat to right itself completely within 20 seconds of being placed in dorsal recumbency. The duration of LRR is defined as the time interval between LRR and the return of righting reflex.

TABLE 4

Rat Loss of Righting Reflex (LRR)

| | Duration of Rat LRR | Rat Dose |
|---|---|---|
| 29, MQ-97 | B | 15 mg/kg |
| 16, MQ-92 | B | 5 mg/kg |

TABLE 4-continued

| Rat Loss of Righting Reflex (LRR) | | |
|---|---|---|
| | Duration of Rat LRR | Rat Dose |
| 8, MQ-89 | C | 15 mg/kg |
| 17, MQ-93 | C | 15 mg/kg |
| 20, MQ-98 | A | 15 mg/kg |

A <10 min; B 10-20 min; C >20 min.

F. Dog Loss of Lateral Recumbence

The plasma pharmacokinetics and a qualitative assessment of sedation were obtained in male beagle dogs according to the following procedure. Dogs were dosed by intravenous bolus dose (60 seconds) via the cephalic vein at 5 mg/kg dose in an appropriate vehicle. In order to assess sedation, dogs were gently restrained for dose administration. If decreased muscle tone, limb weakness, or head drop was observed during dose administration, onset of lateral recumbence was recorded. In the event that lateral recumbence did not occur during dosing, the animals were evaluated at 5 minute intervals thereafter by being placed in lateral recumbence. Sluggish or incomplete righting to the sternal position qualifies as lateral recumbence. After onset of lateral recumbence, animals were assessed every 5 minutes in the same manner. The duration of lateral recumbence was recorded as the time interval between onset of lateral recumbence and the return to sternal position.

TABLE 5

| Dog Duration of Lateral Recumbence | | |
|---|---|---|
| | Duration of Dog Lateral Recumbence | Dog Dose |
| 29, MQ-97 | C | 5 mg/kg |
| 16, MQ-92 | B | 5 mg/kg |
| 8, MQ-89 | C | 5 mg/kg |

A <10 min; B 10-20 min; C >20 min.

General Methods

The compounds discussed in the present disclosure were produced as discussed elsewhere throughout this disclosure and by the following methods.

Solvents were either used as purchased or dried and purified by standard methodology. Extraction solvents were dried with anhydrous $Na_2SO_4$ and after filtration, removed on a rotary evaporator. Flash chromatography was performed using silica gel (32-63 μm) purchased from Scientific Adsorbents (Atlanta, Ga.). Melting points were determined on a Kofler micro hot stage and are uncorrected. FT-IR spectra were recorded as films on a NaCl plate. NMR spectra were recorded in $CDCl_3$ at ambient temperature at 300 MHz ($^1H$) or 74 MHz ($^{13}C$). Purity was determined by TLC on 250 μm thick Uniplates™ from Analtech (Newark, Del.). All pure compounds (purity>95%) gave a single spot on TLC. Elemental analyses were performed by M-H-W Laboratories (Phoenix, Ariz.).

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:

1. A method of inducing anesthesia in a subject in need thereof, said method comprising administering to the subject a therapeutically effective amount of a compound of Formula (I-g):

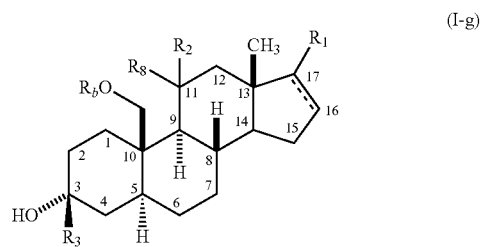

or a pharmaceutically acceptable salt thereof;
wherein:
$R_1$ is selected from ($C_1$-$C_4$ alkyl)-O, spirooxirane, cyano, =O, nitro, ($C_1$-$C_4$ alkyl)C(O), and HO($C_1$-$C_4$ alkyl)C(O);
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_3$ is H, optionally substituted $C_1$-$C_4$ alkyl, optionally substituted $C_2$-$C_4$ alkenyl, optionally substituted $C_2$-$C_4$ alkynyl, or optionally substituted aryl;
$R_b$ is methyl;
$R_8$, when present, is H or optionally substituted $C_1$-$C_4$ alkyl;
- - - denotes an optional, additional C—C bond, resulting in a C=C bond between $C_{16}$-$C_{17}$, with the proviso that when present, the $R_1$ is not =O or spirooxirane.

2. A method of inducing anesthesia in a subject in need thereof, said method comprising administering to the subject a therapeutically effective amount of a compound of the formula:

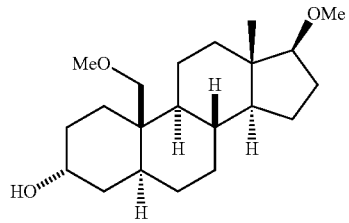

or a pharmaceutically acceptable salt thereof.

3. A method of inducing anesthesia in a subject in need thereof, said method comprising administering to the subject a therapeutically effective amount of a compound of the formula:

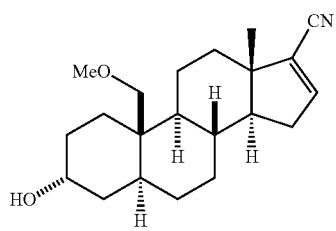

or a pharmaceutically acceptable salt thereof.

4. A method of inducing anesthesia in a subject in need thereof, said method comprising administering to the subject a therapeutically effective amount of a compound of the formula:

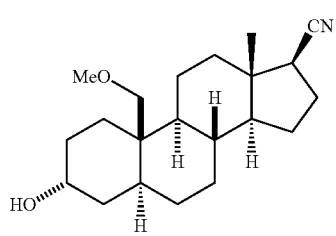

or a pharmaceutically acceptable salt thereof.

5. A method of inducing anesthesia in a subject in need thereof, said method comprising administering to the subject a therapeutically effective amount of a compound of the formula:

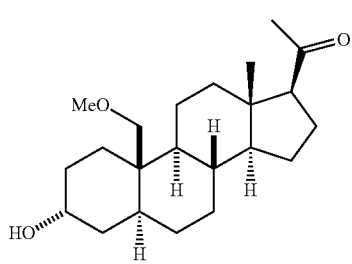

or a pharmaceutically acceptable salt thereof.

6. A method of inducing anesthesia in a subject in need thereof, said method comprising administering to the subject a therapeutically effective amount of a compound of the formula:

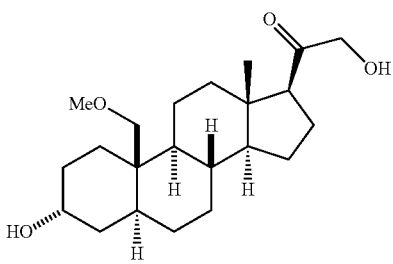

or a pharmaceutically acceptable salt thereof.

7. A method of inducing anesthesia in a subject in need thereof, said method comprising administering to the subject a therapeutically effective amount of a compound of the formula:

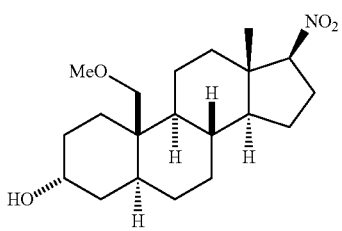

or a pharmaceutically acceptable salt thereof.

* * * * *

UNITED STATES PATENT AND TRADEMARK OFFICE
CERTIFICATE OF CORRECTION

PATENT NO. : 9,676,812 B2  
APPLICATION NO. : 14/652717  
DATED : June 13, 2017  
INVENTOR(S) : Covey et al.

Page 1 of 1

It is certified that error appears in the above-identified patent and that said Letters Patent is hereby corrected as shown below:

In the Specification

Column 1, Line 14, delete "which is are" and insert therefor -- which are --.

Column 1, Lines 19-22, delete "The claimed subject matter was developed with Government support under NIH Grant #GM47969, awarded by the National Institute of Health. Accordingly, the Government has certain rights in the claimed subject matter." and insert therefor -- This invention was made with government support under grant NIH GM047969, awarded by the U.S. National Institutes of Health. The government has certain rights in the invention. --.

Column 3, Line 57, delete "between C4-05 or C5-C6," and insert therefor -- between C4-C5 or C5-C6, --.

Column 8, Line 40, delete "between C4-05." and insert therefor -- between C4-C5. --.

Column 33, Line 22, delete "sodium bisulfate," and insert therefor -- sodium bisulfite --.

Column 52, Line 39, delete "IR $v_{mar}$ 3436, 2921," and insert therefor -- IR $v_{max}$ 3436, 2921, --.

Column 53, Line 6, delete "vma, 3420," and insert therefor -- vmax, 3420, --.

Column 55, Line 67, delete "IR v. 3337" and insert therefor -- IR vmax, 3337 --.

Column 67, Line 1, delete "B. I35S1-TBPS Displacement" and insert therefor -- B. [35S] - TBPS Displacement --.

Signed and Sealed this  
Twelfth Day of December, 2017

Joseph Matal  
*Performing the Functions and Duties of the*  
*Under Secretary of Commerce for Intellectual Property and*  
*Director of the United States Patent and Trademark Office*